(12) United States Patent
Zhao et al.

(10) Patent No.: US 10,748,656 B1
(45) Date of Patent: Aug. 18, 2020

(54) POPULATION HEALTH PLATFORM

(71) Applicant: Harmonize Inc., Pacifica, CA (US)

(72) Inventors: Kevin Zhao, Pacifica, CA (US);
Juvairiya Saidu Pulicharam, Rolling Hills Estates, CA (US)

(73) Assignee: Harmonize Inc., San Mateo, CA (US)

( * ) Notice: Subject to any disclaimer, the term of this patent is extended or adjusted under 35 U.S.C. 154(b) by 0 days.

(21) Appl. No.: 16/442,277

(22) Filed: Jun. 14, 2019

Related U.S. Application Data

(60) Provisional application No. 62/817,486, filed on Mar. 12, 2019.

(51) Int. Cl.
*G16H 40/67* (2018.01)
*G16H 10/60* (2018.01)
*G08B 21/02* (2006.01)
*G16H 50/20* (2018.01)
*G06K 7/14* (2006.01)

(52) U.S. Cl.
CPC .............. *G16H 40/67* (2018.01); *G08B 21/02* (2013.01); *G16H 10/60* (2018.01); *G16H 50/20* (2018.01); *G06K 7/1417* (2013.01)

(58) Field of Classification Search
USPC ....................................................... 705/2, 3
See application file for complete search history.

(56) References Cited

U.S. PATENT DOCUMENTS

| 5,920,263 | A | 7/1999 | Huttenhoff et al. |
|---|---|---|---|
| 8,165,893 | B1 | 4/2012 | Goldberg et al. |
| 9,368,014 | B1 * | 6/2016 | Bittnnan; Barry B ........................ G08B 21/0453 |
| 2008/0077435 | A1 | 3/2008 | Muradia |
| 2008/0288023 | A1 | 11/2008 | John |
| 2010/0218132 | A1 * | 8/2010 | Soni ........................ G01N 33/49 715/771 |
| 2011/0021140 | A1 | 1/2011 | Binier |
| 2012/0221634 | A1 * | 8/2012 | Treu .................... G06F 19/3418 709/203 |
| 2012/0259652 | A1 | 10/2012 | Mallon et al. |

(Continued)

OTHER PUBLICATIONS

Fomichev et al., "Survey and Systematization of Secure Device Pairing," IEEE Communications Surveys & Tutorials, vol. 20, No. 1, First Quarter 2018, pp. 517-550 (Year: 2018).*

(Continued)

*Primary Examiner* — Aryan E Weisenfeld
*Assistant Examiner* — Joshua B Blanchette
(74) *Attorney, Agent, or Firm* — Wilson Sonsini Goodrich & Rosati

(57) ABSTRACT

The present disclosure provides systems, methods, and kits for collecting health measurement data and processing the health measurement data to generate alerts and modify patient treatment plans. An example system can be configured to (i) receive data defining a plurality of health sensors; and (ii) generate, based on the data, application logic configured to cause, in response to one user input, a user device to: (a) couple to the plurality of health sensors, thereby establishing communication between the user device and each of the plurality of health sensors, and (b) provide instructions to a user of the user device through an interface of the user device. The instructions can comprise instructions for taking health measurements using the plurality of health sensors.

27 Claims, 17 Drawing Sheets

(56) References Cited

U.S. PATENT DOCUMENTS

| | | | |
|---|---|---|---|
| 2012/0266251 A1* | 10/2012 | Birtwhistle | H04W 12/003 |
| | | | 726/26 |
| 2013/0093829 A1* | 4/2013 | Rosenblatt | G16H 20/40 |
| | | | 348/14.01 |
| 2013/0162160 A1* | 6/2013 | Ganton | H04M 3/00 |
| | | | 315/210 |
| 2014/0067426 A1 | 3/2014 | Neff | |
| 2014/0118159 A1 | 5/2014 | Fish et al. | |
| 2014/0121487 A1 | 5/2014 | Faybishenko et al. | |
| 2014/0275824 A1 | 9/2014 | Couse | |
| 2014/0378863 A1 | 12/2014 | Schafer | |
| 2015/0112452 A1* | 4/2015 | He | A61B 5/0285 |
| | | | 700/11 |
| 2015/0370994 A1 | 12/2015 | Madan et al. | |
| 2017/0012929 A1* | 1/2017 | Shah | H04L 67/02 |
| 2017/0140120 A1 | 5/2017 | Thrower | |
| 2017/0351504 A1* | 12/2017 | Riedl | G06F 3/002 |
| 2018/0035927 A1 | 2/2018 | Cronin et al. | |
| 2018/0122509 A1 | 5/2018 | Christiansson | |
| 2018/0192965 A1 | 7/2018 | Rose et al. | |
| 2018/0336530 A1* | 11/2018 | Johnson | G06Q 10/1093 |
| 2019/0109822 A1* | 4/2019 | Clark | H04L 63/0236 |

OTHER PUBLICATIONS

Fonnichev et al., "Survey and Systematization of Secure Device Pairing," IEEE Communications Surveys & Tutorials, Vol. 20, No. 1, First Quarter 2018, pp. 517-550 (Year: 2018).*
PCT/US2020/022158 International Search Report and Written Opinion dated Jun. 12, 2020.

* cited by examiner

| | Home | Escalated | Alerts | Add Patient | Logout |
|---|---|---|---|---|---|

DHCP572

Dashboard

Alerts

Diseases

Annotations

Status

Add Measurement

Export

DHCP572

ALERTID: 1772  STATUS: Resolved  DATE CREATED: 5/23/2019 2:10:00 PM

Chloe Ramirez

Alert History

| Event Date | Component Type | Notes | User |
|---|---|---|---|
| 5/23/2019 3:22:32 PM | Notes | Alert Assigned to Sherry Gordon | Sherry.l.gordon |
| 5/23/2019 3:23:04 PM | Notes | Alert Assigned to Chloe Ramirez | Chloe.delgadoramirez |
| 5/23/2019 4:33:00 PM | SPO2?? | Patient did not want to recheck her O2. Patient stated that she is very sick and is starting antibiotics today. Will escalate to Dr. for further follow up. | Chloe.delgadoramirez |
| 5/23/2019 4:43:00 PM | BloodPressureSys | Patient rechecked BP | Chloe.delgadoramirez |
| 5/23/2019 4:52:15 PM | Status Changed | Escalated | Chloe.delgadoramirez |
| 5/23/2019 | Notes | Patient alerted for LOW O2 | Chloe.delgadoramirez |

FIG. 10C

| | Home | Escalated | Alerts | Add Patient | | Logout |
|---|---|---|---|---|---|---|
| | | | | | | Chloe.delgadoramirez |
| DHCP572 | 5/23/2019 4:52:15 PM | Notes | Patient Alerted for LOW O2<br>Patient Name:<br>MRN:<br>DOB:<br>PHONE:<br>PCP:<br>Comorbidities: HTN, CHF, DM<br>Medication List:<br>1. Accu-Chek Compact Plus In Vitro Strip; USE 1 STRIP 3 TIMES DAILY; Therapy: 27Jan2015 (Evaluate:02Jul2019) Requested for: 03Jan2019; Last Rx: 03Jan2019 Ordered Rx By: RUSS, ROBERT: Dispense: 90 Days ; #:270 Strip; Refill: 1;for: Diabetic peripheral Neuropathy, PMI: type 2 diabetes, uncontrolled, with neuropathy: DAW = N; Verified Transmission to HUMANA PHARMACY MAIL; Last Updated By: System SureScripts; 1/3/2019 5:57:54PM<br>2. Advair Diskus 250-50 MCG/DOSE Inhalation Aerosol Powder Breath Activated (Fluticasone-Salmeterol): inhale 1 puff twice daily: Therapy: 18Jun2018 to (Last Rx:03Jan2019) requested for: 03Jan2019 Ordered Rx By: RUSS, ROBERT; Dispense: 0 Days : #:180 Each: Refill: 1:For: Chronic obstructive Pulmonary disease: DAW =N; Verified Transmission to HUMANA PHARMACY MAIL DELIVERY-RSRX; Last Updated By: System, SureScripts; 1/3/2019 5:57:52 PM<br>3. ALPRAZolam 0.5 MG Oral Tablet: TAKE 1 TABLET DAILY AS NEEDED: Therapy; 29Mar2017 to (Evaluate:06Jan2018); Last Rx: 07Dec2017 Ordered Rx By: MARDING-INACTIVE, EDWARD: Dispense: 30 Days ; #:30 Tablet; Refill: 0;For: Anxiety; DAW = n; Print Rx<br>4. 80 Insulin Syringe Ultrafine 31G x 5/16" 0.5 ML; use as directed three times daily; Therapy: 12Aug2015 to (Last Rx: 03Jan2019) Requested for: 03Jan2019 Ordered Rx By: RUSS, ROBERT: Dispense: 0 Days : #:300 Each; Refill: 1;For: Diabetic peripheral Neuropathy, PMH: Type 2 diabetes, uncontrolled, with neuropathy: DAW = N; Verified Transmission to HUMANA PHARMACY MAIL DELIVERY-RSRX; Last Updated By: System, SureScripts; 1/3/2019 5:57:58PM | | |
| Dashboard | | | | | | |
| Alerts | | | | | | |
| Diseases | | | | | | |
| Annotations | | | | | | |
| Status | | | | | | |
| Add Measurement | | | | | | |
| Export | | | | | | |

FIG. 10D

POPULATION HEALTH PLATFORM

CROSS-REFERENCE

This application claims priority to U.S. Provisional Patent Application No. 62/817,486, filed on Mar. 12, 2019, which is entirely incorporated herein by reference.

BACKGROUND

Multi-sensor monitoring systems can include a central computing device and various peripheral sensors. The central computing device can act as a data aggregator for the peripheral sensors. Conventional multi-sensor monitoring systems can require significant user setup. For example, a user may need to connect the central computing device and each peripheral sensor to a network, and manually pair each peripheral sensor to the central computing device over the network. This process can be burdensome to users in demographics that are not technologically savvy. Conversely, some multi-sensor monitoring systems may have a streamlined pairing workflow that is hard-coded to pair a specific set of peripheral sensors to the central computing device. However, hard-coding can result in an inflexible sensor combination that cannot be dynamically changed across multiple users of the multi-sensor monitoring system. Changes to a hard-coded system can require full code recompilations and new application releases for each user, which can make it difficult to scale the multi-sensor monitoring system.

Multi-sensor monitoring systems can include health sensor systems. Many health sensor systems may not transform collected data into health outcomes for patients. Health sensor systems that use remote monitoring technology may rely on human interpretation of health sensor data, or they may manually inject health sensor data from many vertically integrated sensor systems (e.g., distinct oxygen sensing and glucose sensing systems) into a separate third-party analytics provider. Afterwards, the health sensor systems may then provide the output of these analytics to service providers (e.g., emergency response services, therapeutics companies, etc.). Currently, no system exists that agnostically connects health sensor systems to analytics that detect patient deteriorations and interventional services that address such deteriorations. Furthermore, no system performs the aforementioned steps in a continuous loop to iterate upon its automated decision making processes. The lack of such a system introduces labor inefficiencies and translational costs for today's medical providers.

SUMMARY

The present disclosure describes a customizable population health system, and corresponding methods and kits, that can (i) automatically configure health sensors, (ii) take health measurements using the health sensors, (iii) automatically manage and process data generated by the health sensors, (iv) and automatically utilize processed data to generate alerts and inform and/or modify treatment or behavioral plans. The population health system can be personalized to each user, and can horizontally integrate sensors, algorithms, and therapeutic services that can be connected into a custom-tailored portfolio for each user of the system.

Specifically, the systems, methods, and kits described in the present disclosure can automatically pair, setup, and configure a user-specific combination of health sensors to a user device on which a health application is installed, thereby establishing wireless communication between the health sensors and the user device, without any required interaction from the user. The system can then instruct the patient to take health measurements using the health sensors and obtain data generated by those health sensors with minimal user input.

Data obtained from the sensors can be automatically be transmitted to a cloud-based platform of the population health system, where the data can be processed using a user-specific analytics portfolio that can either be pre-selected by a healthcare provider or automatically selected based on the system's own artificial intelligence. Once data is processed, the system can automatically route select data outputs to the patient, the patient's healthcare provider, or a user-specific combination of third party service providers (e.g., emergency response services, therapeutics services, health coaches, etc.).

As a whole, the system can obtain sensor data and make data-driven therapeutic decisions including the likes of medication titration, enforcing medication adherence, and enforcing behavioral/lifestyle adherence. For each user of the system, system can capture results of health outcomes and continuously iterate upon itself as a user's health state changes dynamically.

For patients who do not have a mobile computing device or who struggle navigating mobile operating systems, the above-mentioned heath application can be deployed on an electronic tablet that is shipped alongside the health sensors in a customizable kit. A health care provider can determine the particular set of health sensors in the kit based on the patient's medical needs. The health application deployed on the electronic tablet can be configured with a "workflow" that corresponds to the particular set of heath devices in the kit. The workflow can be a set of procedures, i.e., processing logic, that can cause the electronic tablet to automatically pair to the heath sensors over a network without requiring any user interaction, provide instructions about how to use each of the health sensors to take health measurements, obtain health measurement data generated by those health sensors, and parlay processed data results (visual and/or audio) back to the user for education and/or therapeutic feedback. The workflow can be assembled in a modular fashion from pre-defined processing logic. If the health care provider prescribes additional health sensors to his or her patient, the patient can receive another shipment with the additional health sensors. The workflow on the patient's health application can be automatically reconfigured, e.g., over the cloud, to account for the patient's new combination of health sensors.

Patients who have their own mobile computing device can instead download the health application from the Apple App Store or the Google Play Store. Along with a shipment of health sensors prescribed by a health care provider, such patients can receive a barcode or a quick response (QR) code that defines the unique combination of health sensors in the shipment. The patient can scan the QR code using the mobile computing device, and the health application can configure its workflow based on the data encoded in the QR code. Alternatively, the health care provider can upload an electronic treatment plan to a cloud-based platform of the population health system. The electronic treatment plan can define the unique combination of health sensors prescribed to the patient by the health care provider. The electronic treatment plan can be associated with a health profile of the patient to which the health care provider has access. The health application can synchronize the patient's health profile, including the electronic treatment plan, between the platform and the user device. The health application can use the electronic treatment plan to generate a workflow corresponding to the unique combination of health sensors prescribed by the health care provider.

The health sensors can include continuous sensors that obtain time-series data over a period of hours. The continuous sensors can be wearable devices, for example. The health sensors can also include single-use sensors that obtain a single health measurement in a finite period of time. The health sensors can include heart rate monitors, blood pressure devices, pulse oximeters, scales, thermometers, glucose meters, and the like.

The workflow can cause the user device to automatically pair the health sensors to the user device when the health sensors are (a) on and (b) within range of the user device, thereby establishing wireless communication between the health sensors and the user device. The wireless communication can be established over a Bluetooth network or a Wi-Fi network, for example.

Automatically pairing the health sensors to the health application can involve selecting, from a database of predefined pairing procedures, a pairing procedure for each health sensor in the unique combination. The automatic pairing can additionally involve obtaining a universally unique identifier for each of the health sensors in the unique combination, and using the universally unique identifiers to scan and identify the health sensors. The workflow can also handle setting up and configuring secure connections and passkey-based pairing.

The workflow can also cause the user device to provide instructions to a patient through a graphical user interface of the health application in response to a user input. The instructions can be instructions for taking health measurements using the health sensors, e.g., instructions that indicate how to use the health sensors. The instructions can be audible, textual, pictorial, animations, or the like.

The health application can automatically provide instructions for taking a particular health measurement using a particular health sensor after receiving valid data for a preceding health measurement, without further user input. In this way, patient interaction with the health application can be minimized. Valid data can be data that falls within a predefined range, or it can be data that has a particular characteristic. The health application can also provide control signals to the health sensors. For example, after determining that a patient is properly using or wearing a particular health sensor, the health application can automatically transmit a control signal to the health sensor that causes the health sensor to take the health measurement. This can further minimize patient interaction with both the health application and the health sensors.

The health application can obtain health measurement data generated by the health sensors. The health application can store the health measurement data to the patient's health profile on the platform. The system can automatically monitor the patient's health by inputting the data into a customizable sequence of algorithms. The sequence of algorithms can be automatically changed by the system as a patient's health state changes or can be modified by the patient's health care provider at any time. The outputs of such processing can be extrapolated into alerts, essential vitals, and trends. These outputs can be conveyed in real time to health care providers and third party service providers. This can ensure that the patient receives timely medical care in the case of abnormal health measurements and/or irregular health trends.

The portfolio of algorithms and third party service providers can be customized for each patient health profile. This can be especially useful for treating patients with multiple comorbidities (chronic disease states). For example, a patient with chronic obstructive pulmonary disorder (COPD), arterial fibrillation, and hypertension can have a profile of algorithms that determine likelihood for arrhythmias and oxygenation/ischemic-related episodes. The service providers for such a patient may include emergency responders, health coaches, and cardiologists. A patient with diabetes and chronic heart failure, on the other hand, may have a set of algorithms that detect for the onset of diabetic-related edema development and glucose instability. The service providers for such a patient may include endocrinologists, pharmacists, and therapeutics companies.

As a result of horizontally integrating customizable portfolios of sensors, analytics, and service providers, the system as a whole can make data-driven therapeutic decisions including the likes of medication titration, enforcing medication adherence, and enforcing behavioral/lifestyle adherence. In the case of medication titration, the system can monitor the effects of prescribed medication on a user's chronic illness states. If the prescribed medication for one condition (e.g., diabetes) causes the symptoms of another coexisting condition (e.g., hypertension) to get worse, the system can automatically titrate the user's medication prescription to adjust for these effects. In the case of medication adherence, the system can detect when patients do not take their medications and/or perform vital measurements in a timely manner, and issue visual and/or audio warnings (e.g., notifications, phone calls, etc.) to remind the user to adhere to medicinal protocol. If a user's non-adherence to medication causes a severe drop in the user's health state, the system can notify third party services to check in on the user. In the case of lifestyle and behavioral adherence, the system can detect behavioral nonadherence (e.g., diabetics eating candy at night or COPD patients not wearing their oxygen masks) and issue warnings (e.g., through notifications, phone calls, and/or service providers) for patients to rectify behaviors that may damage their health.

The systems, methods, and kits described above can allow patients who are not technologically savvy to easily obtain health measurement data from patient-specific portfolios of health sensors from the comfort of their homes, and while requiring minimal user input. Usability studies show that the target demographic may not want to setup, pair, and control each health sensor individually. Instead, these patients may prefer to have minimal interaction with both the health application and the health sensors. In addition to providing a seamless health measurement experience with minimal user input, the health application can handle end user chaos. For example, the health application can handle data that is cached on a health sensor when a patient walks out of range of that health sensor during a data upload. The health application can also detect if a patient is using a health sensor improperly and provide guidance to optimize the patient's usage. This can ensure that the patient takes all measurements in a medically-accurate manner. The ease of use of the system can result in greater patient adherence to health measurement routines.

Data acquired by the health application can be injected into the rest of the system. Upon injection, the system can run the data through patient-specific portfolios of algorithms in order to generate processed data outputs. The procedure of generating such outputs can include, but is not limited to, filtering out excess and/or noisy data, extrapolating a patient's essential vitals, identifying key trends, and generating alerts. The generation of alerts can reduce hospitalizations through timely intervention. The processed data can then be parlayed to patient-specific portfolios of service providers within the system, which can include the likes of therapeutics services, behavioral services, and physicians.

As an integrated whole, the system can make important therapeutic interventions and medicinal titrations to positively impact a patient's health outcomes. This is especially beneficial to high risk patients with multiple comorbidities who need multiple medical sensors to monitor their health states, carefully balanced medication titrations, and non-conflicting therapeutic care (one intervention for a disease state doesn't aggravate another coexisting disease state) in order to prevent rehospitalization and/or episodic attacks. To accommodate for the sensitivity and precision required for treating such high risk patients, the system can gather the entire cascade of health results, ranging from sensor data inception all the way to the health outcomes as a result of interventions, and iterate and adjust itself in order to adapt to each patient's dynamically changing health state.

The integrated, end-to-end nature of the system can increase throughput and reduce costs for major health care providers.

In an aspect, a population health system can be configured to perform operations comprising: receiving data defining a plurality of health sensors; and generating, based on the data, a workflow for an application on a user device, wherein the workflow is configured to cause the user device to: (i) automatically pair the plurality of health sensors to the user device when the plurality of health sensors are (a) on and (b) within range of the user device, thereby establishing wireless communication between the plurality of health sensors and the user device, and (ii) provide instructions to a user through a graphical user interface of the application in response to a user input, the instructions comprising instructions for taking health measurements using the plurality of health sensors, wherein the application is configured to obtain health measurement data from each of the plurality of health sensors without additional user input.

In some embodiments, the system comprises a cloud-based platform. In some embodiments, the operations further comprise storing the health measurements in the cloud-based platform. In some embodiments, the cloud-based platform comprises a health care profile for each of a plurality of users. In some embodiments, receiving data defining a plurality of health sensors comprises receiving an electronic treatment plan prescribing the plurality of health sensors to a given user of the plurality of users through the cloud-based platform. In some embodiments, the electronic treatment plan is associated with a health care profile of the given user on the cloud-based platform. In some embodiments, the health care profile of the given user is accessible to one or more health care providers of the user. In some embodiments, the application is configured to communicate an electronic alert to the health care provider when any one of the health measurements of the given user falls outside of a predefined range.

In some embodiments, receiving data defining a plurality of health sensors comprises receiving an image of a barcode defining the plurality of health sensors. In some embodiments, the barcode is a QR code.

In some embodiments, the plurality of health sensors are selected from the group consisting of a heart rate monitor, a blood pressure cuff, a pulse oximeter, a scale, a thermometer, and a glucose meter. In some embodiments, the plurality of health sensors comprises one or more continuous sensors. In some embodiments, the one or more continuous sensors comprise a wearable device. In some embodiments, the plurality of health sensors comprises one or more spot-check sensors.

In some embodiments, the operations further comprise receiving an order of the plurality of health sensors, wherein the instructions for taking the health measurements using the plurality of health sensors are provided to the user in the order.

In some embodiments, generating the workflow comprises selecting, from a plurality of pre-defined pairing procedures, a pairing procedure for each the plurality of health sensors. In some embodiments, generating the workflow comprises obtaining, from a configuration file, a universally unique identifier for each of the plurality of health sensors. In some embodiments, the automatic pairing comprises scanning and identifying the plurality of health sensors defined by the data.

In some embodiments, the workflow is further configured to cause the user device to transmit control signals to the plurality of health sensors to control operation of the health sensors during the health measurements.

In some embodiments, the wireless communication is established over a Bluetooth network. In some embodiments, the wireless communication is established over a Wi-Fi network. In some embodiments, the instructions comprise animations that indicate how to use the plurality of health sensors.

In some embodiments, the instructions comprise audible instructions. In some embodiments, the instructions comprise textual instructions. In some embodiments, the instructions comprise pictorial instructions. In some embodiments, the application is configured to provide instructions for taking a given heath measurement using a given health sensor after receiving valid data for a preceding health measurement. In some embodiments, valid data comprises data falling within a predefined range. In some embodiments, valid data comprises data having a predetermined characteristic.

Another aspect of the present disclosure provides a kit comprising a plurality of health sensors and a user device configured to run an application, wherein the application is configured to cause the user device to perform the operations described above.

Another aspect of the present disclosure provides a method comprising the operations described above.

In another aspect, the present disclosure provides a system that can receive data defining a plurality of health sensors. The system can generate, based on the data, application logic configured to cause, in response to one user input, a user device to: (a) couple to the plurality of health sensors, thereby establishing communication between the user device and each of the plurality of health sensors, and (b) provide instructions to a user of the user device through an interface of the user device. The instructions can comprise instructions for taking health measurements using the plurality of health sensors.

In some embodiments, the system can obtain health measurement data from the user device. The health measurement data can comprise data collected as a result of the user taking the health measurements. The system can determine that the health measurement data satisfies an alert criterion. In response to the determination, the system can transmit an alert to a health care provider of the user.

In some embodiments, prior to transmitting the alert, the system can classify the alert as a low-priority alert, a medium-priority alert, or a high-priority alert. Transmitting the alert to the health care provider can comprise: (i)

transmitting a low-priority alert to a behavior intervention service, (ii) transmitting a medium-priority alert to an in-home health service, and (iii) transmitting a high-priority alert to a primary care physician of the user or an emergency service.

In some embodiments, transmitting the high priority alert to the primary care physician or the emergency service can comprise transmitting an escalation report to the primary care physician or the emergency service.

In some embodiments, the escalation report can comprise a subset of the medical history data for the patient and the health measurement data.

In some embodiments the classifying can comprise obtaining medical history data for the patient and using a trained machine learning algorithm to process the health measurement data and the medical history data to generate the classification.

In some embodiments, the trained machine learning algorithm can be selected from the group consisting of: a regression algorithm, a Naive Bayes classifier, a support vector machine, a clustering algorithm, a decision tree algorithm, a random forest, or a neural network.

In some embodiments, receiving data defining the plurality of health sensors can comprise receiving an electronic treatment plan prescribing the plurality of health sensors to the user from a primary care physician of the user.

In some embodiments, receiving data defining the plurality of health sensors can comprise receiving an image of a barcode defining the plurality of health sensors. The barcode can be a QR code.

In some embodiments, the plurality of health sensors can be selected from the group consisting of a heart rate monitor, a blood pressure cuff, a pulse oximeter, a scale, a thermometer, and a glucose meter.

In some embodiments, the system can receive an order of the plurality of health sensors. The application logic can be configured to provide the instructions for taking the health measurements in the order.

In some embodiments, generating the application logic can comprise selecting, from a plurality of pre-defined pairing procedures, a pairing procedure for each of the plurality of health sensors.

In some embodiments, generating the application logic can comprise obtaining, from a configuration file, a universally unique identifier for each of the plurality of health sensors.

In some embodiments, the coupling can comprise scanning and identifying the plurality of health sensors defined by the data.

In some embodiments, the application logic can be further configured to cause the user device to transmit control signals to the plurality of health sensors to control operation of the plurality of health sensors during the health measurements.

In some embodiments, the application logic can be a module of a health application installed on the user device. The health application can comprise a communication interface configured to allow the user to communicate with a health care provider.

In some embodiments, the instructions can comprise animations that indicate how to use the plurality of health sensors.

In some embodiments, the instructions can comprise audible instructions, textual instructions, or pictorial instructions.

In some embodiments, the application logic can be configured to provide instructions for taking a heath measurement using a health sensor after receiving valid data for a preceding health measurement.

In some embodiments, valid data can comprise data falling within a predefined range or data having a predetermined characteristic.

In some embodiments, the application logic can be configured to provide instructions for re-taking a health measurement after receiving invalid data for the health measurement.

In some embodiments, the data can comprise a time or a measurement frequency associated with a respective health sensor of the plurality of health sensors, and wherein the application logic is configured to provide instructions for taking a health measurement using the respective health sensor at the time or with the measurement frequency.

In some embodiments, the system can store health measurement data from the user device on a cloud-based platform. The health measurement data can comprise data collected as a result of the user taking the health measurements.

In some embodiments, the cloud-based platform can comprise a dashboard configured to allow a health care provider to review the health measurement data.

In some embodiments, the system can receive data indicating a validity of the alert from the health care provider and adjust the alert criterion based on the data indicating the validity of the alert.

Another aspect of the present disclosure provides a kit comprising a plurality of health sensors and a user device configured to run an application, wherein the application is configured to cause the user device to perform the operations described above.

Another aspect of the present disclosure provides a method comprising the operations described above.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 10A-10D are images of an example dashboard of the population health system.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure describes customizable population health system, and corresponding methods and kits, that can (i) automatically configure health sensors, (ii) take health measurements using the health sensors, (iii) manage data generated by the health sensors, (iv) and use the data to generate or modify treatment or behavioral plans. Specifically, the systems, methods, and kits described in the present disclosure can allow a patient to automatically pair a unique combination of health sensors to a user device on which a health application is installed, thereby establishing wireless communication between the health sensors and the user device. The health application can instruct the patient to take health measurements using the health sensors and obtain data generated by heath sensors with minimal user input.

Figure 1:
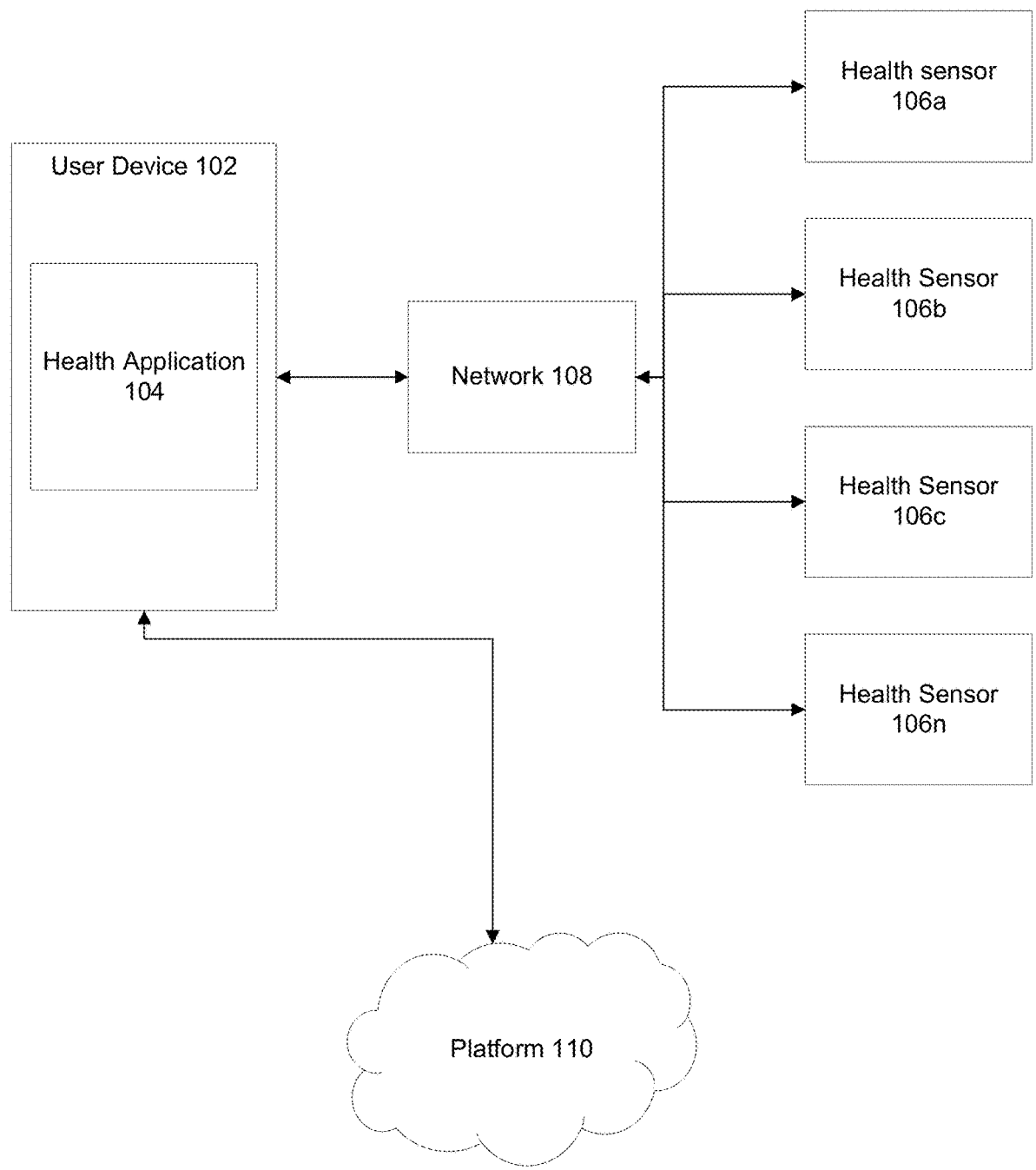
FIG. 1 schematically illustrates a population health system.

FIG. 1 schematically illustrates a population health system. A patient can use the population health system to: (i) take health measurements using health sensors; (ii) obtain, store, and manage data generated by the health sensors; and (iii) use the data to generate alerts or modify treatment or behavioral plans. The population health system can be configured to require minimal user input at all stages of the health measurement process. For example, the population health system can be configured to automatically setup, pair, and control the health sensors. The population health system can also be configured to automatically instruct a patient how to take health measurements and in which order to take those health measurements. Finally, the population health system can be configured to automatically obtain data generated by the health sensors and transmit that data to a platform accessible to a health care provider.

The population health system can include a user device 102. The user device 102 can be any electronic device capable of communicating with other electronic devices over a network, e.g., a Bluetooth network, a Wi-Fi network, the Internet, or the like. For example, the user device 102 can be a laptop or desktop computer, an electronic tablet, a smartphone, a smartwatch, or the like. In some implementations, the user device 102 can be a patient's personal device. In other implementations, the user device 102 can be provided to the patient along with a shipment of health sensors.

The user device 102 can run a health application 104. The health application 104 can be an HTML document rendered by a web-browser, JavaScript code or Java code, or dedicated software, e.g., an installed application. The health application 104 can cause the user device 102 to automatically pair to, i.e., establish a wireless connection with, health sensors 106a-106n over a network 108. Thereafter, the health application 104 can wirelessly communicate with the health sensors 106a-106n. For example, the health application 104 can transmit control instructions to the health sensors 106a-106n and obtain health measurement data from the heath sensors 106a-106n.

Figure 2:
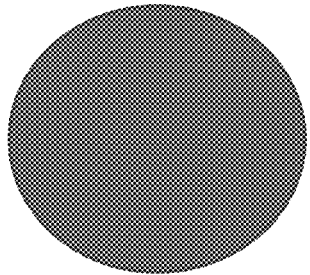
FIG. 2 is a view of a user input feature of a health application of the population health system.

The health application 104 can also be configured to provide instructions to the patient about how to take health measurements using the health sensors and in which order to take the health measurements. In response to a user input, the health application 104 can provide instructions to the patient about how to take a health measurement using a particular health sensor. The user input can be a tap on a capacitive touch screen, a mouse-click, or a voice command, to name a few examples. FIG. 2 is a view of a user input feature of the health application 104. As indicated in FIG. 2, a patient can "Tap the icon to add a measurement."

The instructions can be audible, textual, pictorial, animated, or some combination of these. The health application 104 can include configurable settings that allow a patient to specify the format in which he or she prefers to receive instructions. For example, a patient who is hard-of-hearing may choose to receive visual instructions over audible instructions.

The instructions can indicate which device to use to take the health measurement. The health application 104 can cause the user device 102 to display an image of the health sensor, to say the name of the health sensor, or to describe what the health sensor looks like. The health application 104 can determine that the patient identified and picked up the correct health sensor by detecting motion or a change in position of the health sensor.

The health application 104 can then cause the user device 102 to provide instructions to the patient regarding how the patient should position the health sensor in order to take a proper health measurement. For example, if the health sensor is a blood pressure device, the health application 104 can cause the user device 102 to provide instructions that indicate that the patient should position the blood pressure cuff on his or her upper right arm. As another example, if the health sensor is a pulse oximeter, the health application 104 can cause the user device 102 to provide instructions that indicate that the patient should position the pulse oximeter on his or her left index finger.

The health sensor can include position sensors that collect data regarding the location of the health sensor relative to the patient's body. The health sensor can transmit that data to the health application 104, which can interpret the data to determine whether the heath sensor should be adjusted relative to its current position, or whether it is positioned properly on the patient's body. If the health sensor is not positioned properly, the health application 104 can cause the user device 102 to provide additional, corrective instructions. For example, if the health sensor is a blood pressure device, the health application 104 can cause the user device 102 to provide instructions that indicate that the patient should adjust the position of the blood pressure cuff on his or her arm.

After the health application 104 determines that the health sensor is properly positioned with respect to the patient's body, the health application can transmit control instructions to the health sensor, if necessary. For example, if the health sensor is a blood pressure device, the health application 104 can cause the user device 102 to transmit a control signal to the cuff of the blood pressure device that can cause the cuff to inflate. In some cases, the health application 104 may not transmit control signals to the health sensor. For example, if the health sensor is a heart rate monitor, the heart rate monitor may begin collecting valid data as soon as it is correctly positioned on the patient's body, and it may not need an external control signal to operate. Likewise, passive devices such as scales and thermometers may begin collecting valid data as soon as they are correctly positioned.

While the health sensor obtains data from the patient, the health application 104 can cause the user device 102 to indicate the progress of the health measurement. The indication can be a visual indication, e.g., a progress bar or a textual percentage, or an audible indication of the same.

The health sensor can transmit resultant health measurement data to the user device 102. The health application 104 can determine if the data is valid. Valid data can be data that falls within a predefined range. For example, a valid heart rate may be between 20 beats/minute and 220 beats/minute. If the data falls outside the predefined range, the health application 104 may determine that the health sensor was incorrectly positioned or used, and the health application 104 may instruct the user to take the health measurement again. Valid data can also be data that has a particular characteristic. For example, if the health sensor is a scale, the health application 104 may expect to receive a single data point indicating the patient's measured weight. If the received data is instead time-series data with multiple data points, the health application 104 may determine that the data is invalid, e.g., because the patient used the incorrect health sensor.

When the health application 104 determines that it has received valid data for the health measurement, the health application 104 can cause the user device 102 to provide instructions for taking a second health measurement using a second health sensor. The process described above can be repeated for each of the health sensors in the patient's unique combination of health sensors.

In some cases, instructions for taking a particular health measurement may be provided at a particular time of day, e.g., after the patient has eaten a meal. In such cases, the health application 104 can notify the patient to take the health measurement at that time. The health application 104 can also remind the patient to take measurements that are overdue.

The health application 104 can immediately transmit valid data that it receives from a health sensor to a platform 110. The platform 110 can be implemented on the cloud and can store and process patient data and provide health care professionals access to the data. The platform 110 and portions thereof will be described in greater detail in reference to FIG. 6.

Figure 3:
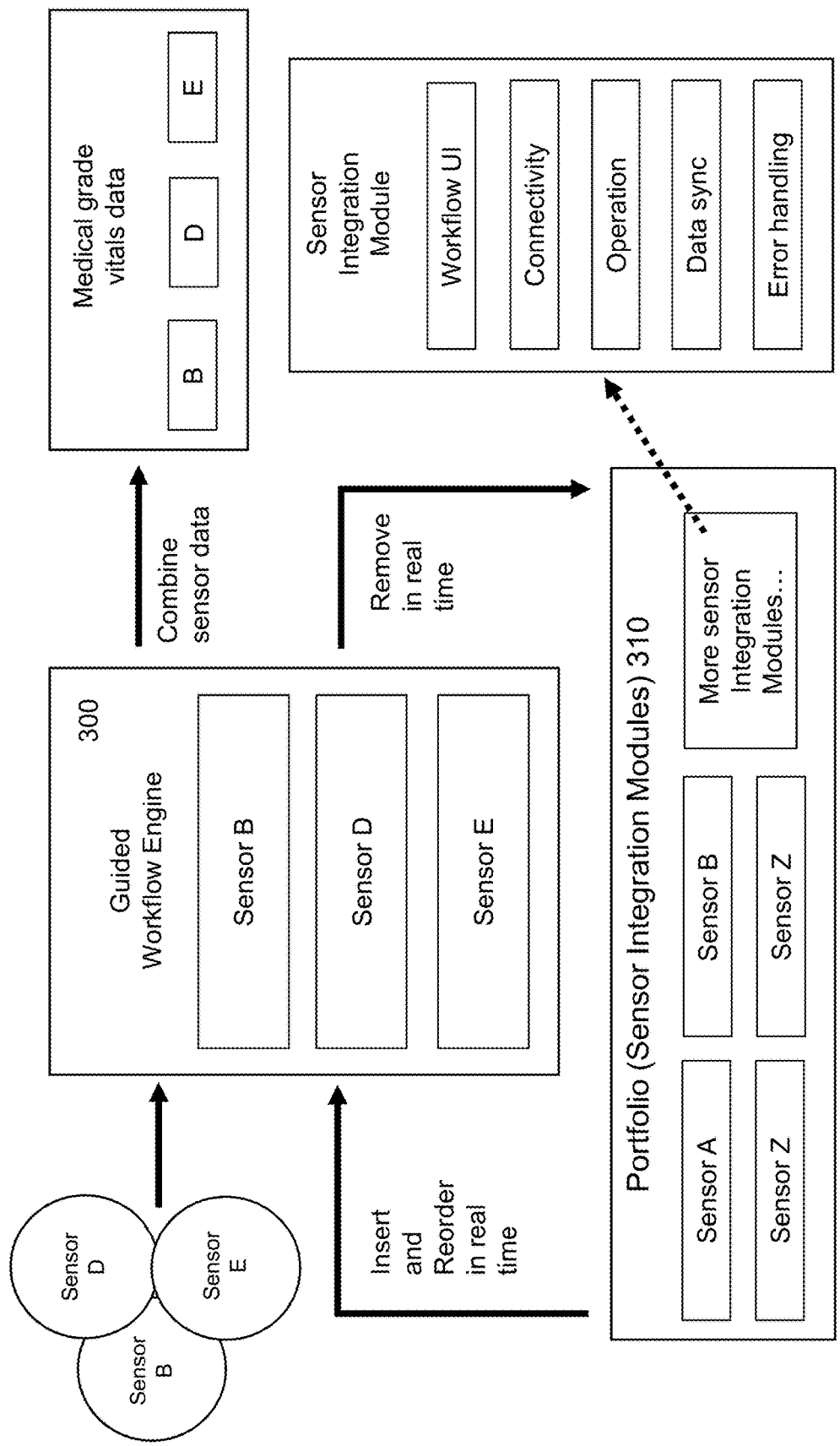
FIG. 3 schematically illustrates a patient-facing layer of the health application.

FIG. 3 schematically illustrates a patient-facing layer of the health application described herein. The patient-facing layer can include a guided workflow engine 300 that can, using a portfolio of sensor integration modules 310, (i) connect the health sensors to the user device on which the health application is installed, (ii) provide patient instructions as described in detail in reference to FIG. 1, (iii) control operation of the health sensors, (iv) transmit and synchronize data between the health sensor, the health application, and the analytics layer, and (v) handle errors that occur at any point in the process.

The portfolio of sensor integration modules 310 can include a sensor integration module for each health sensor in the population health system. Each sensor integration module can include procedures for performing functions (i), (ii), (iii), (iv), and (v) above. For example, the sensor integration module for sensor A can include pre-defined procedures that cause the user device to (i) pair sensor A to the user device, (ii) provide visual or audible instructions about how to use sensor A, (iii) control operation of sensor A after it is properly positioned on the patient's body, (iv) receive health measurement and other data from health sensor A and transmit that data to the platform, and (v) handle any errors that occur while the patient uses sensor A. Each of these functions is described in greater detail below.

Figure 4B:
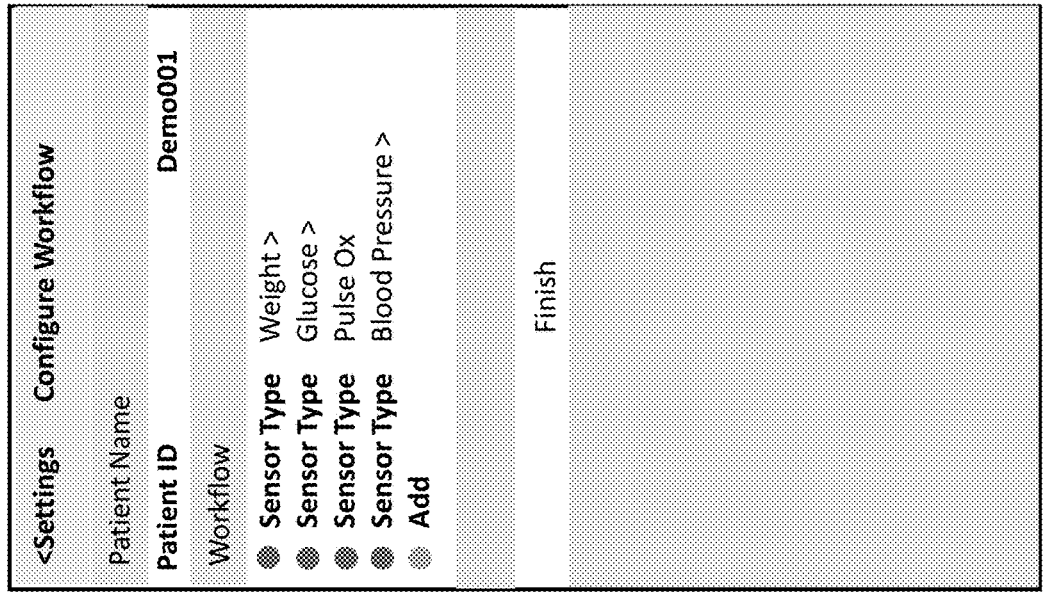
FIGS. 4a and 4b are views of a QR code scanning feature of the health application.
Figure 4A:
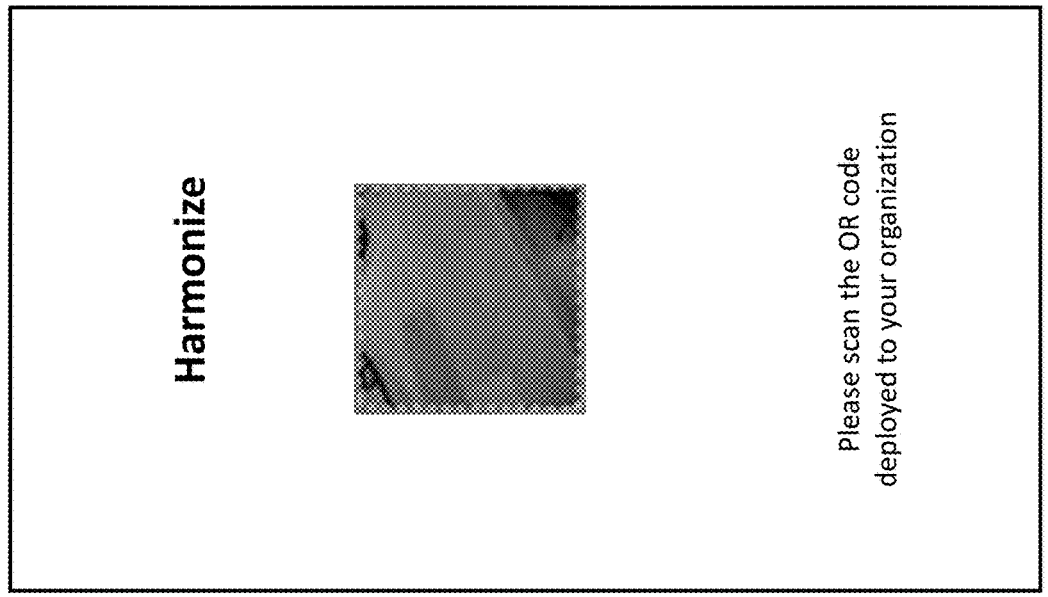

The guided workflow engine 300 can select from the portfolio 310 the particular sensor integration modules that correspond to the health sensors prescribed to the patient by a health care provider. As previously mentioned, the health sensors prescribed to a patient can be defined in an electronic health plan or a QR code. The guided workflow engine 300 can read the electronic health plan or the QR code and integrate the corresponding sensor integration modules into the workflow of the application. FIGS. 4a and 4b are views of a QR code scanning feature of the health application.

In some implementations, the electronic health plan or the QR code can define an order of the prescribed health sensors. In such implementations, in addition to selecting the sensor integration modules from the portfolio 310, the guided workflow engine 300 can arrange the sensor integration modules in the order. This can ensure that the patient takes health measurements in the prescribed order. The electronic health plan or the QR code can also define a measurement frequency for each health sensor, or a time of day that each health sensor should be used. The guided workflow engine 300 can incorporate these conditions into the workflow for the health application, e.g., by providing health measurement instructions to the patient at the defined frequencies or particular time of day.

The ordered combination of sensor integration modules (and the frequency and time of day at which the sensor integration modules are executed) defines the workflow for a given instance of the health application. The workflow can be activated by an initial user input in the health application. In some cases, the initial user input is the only input required to take all prescribed health measurements. In the workflow illustrated in FIG. 3, the initial user input can trigger execution of sensor integration module B. Execution of sensor integration module B can cause the user device on which the health application is installed to pair to sensor B. Next, sensor integration module B can cause the user device to provide instructions to the patient about how to use sensor B, control operation of sensor B, receive health measurement data from sensor B, and transmit that data to the platform. Thereafter, sensor integration module B can pass control to sensor integration module D, which can perform corresponding functions for sensor D. This process can be repeated until the entire workflow is complete. The functions that each sensor integration module can perform are greater detail below.

Health Sensor Pairing

The sensor integration module for a particular health sensor can include a procedure, i.e., processing logic or code, for automatically pairing the health sensor to the user device on which the health application is installed when the health sensor is (i) powered on and (ii) within range of the user device.

The sensor integration module can receive a request for a list of health sensors that are visible to the user device. The request can be a user input. The user input can be, for example, a request to begin a health measurement session.

The request can cause the sensor integration module to activate a communication interface, e.g., a Bluetooth communication interface or a Wi-Fi communication interface, on the user device. Using the communication interface, the sensor integration module can scan for devices in the vicinity that use the same communication interface. The sensor integration module can obtain a list of devices that are visible to the user device. The list of devices can include an identifier, e.g., a MAC address or name, for each of the devices in the list. The sensor integration module for the health sensor can compare the identifiers in the list to a known identifier for the health sensor. If the sensor integration module identifies a match, it can send a connection request to the health sensor. The connection request can include authentication information, e.g., a password, for the health sensor. The user device and the health sensor can establish a cryptographically secure connection by sharing a secure link key. The health sensor and the user device can each store the secure link key. Once the link key is generated, an authenticated Asynchronous Connectionless (ACL) link between the devices can protect exchanged data against eavesdropping. This can ensure that sensitive health measurement data is not stolen. The health sensor and the user device can store the secure link key indefinitely or for a predetermined period of time so that the health sensor and the user device can pair more quickly during subsequent health measurement sessions.

Patient Instructions

The sensor integration module for a health sensor can also include procedures that, when executed, cause the user device to provide instructions about how to use the health sensor. These procedures can be executed after the health sensor is successfully paired to the user device. The user device can provide the instructions through a graphical user interface. For example, the user interface can display animations, textual instructions, or a video about how to use the health sensor. The visual instructions can be accompanied by audible instructions.

Figure 5C:
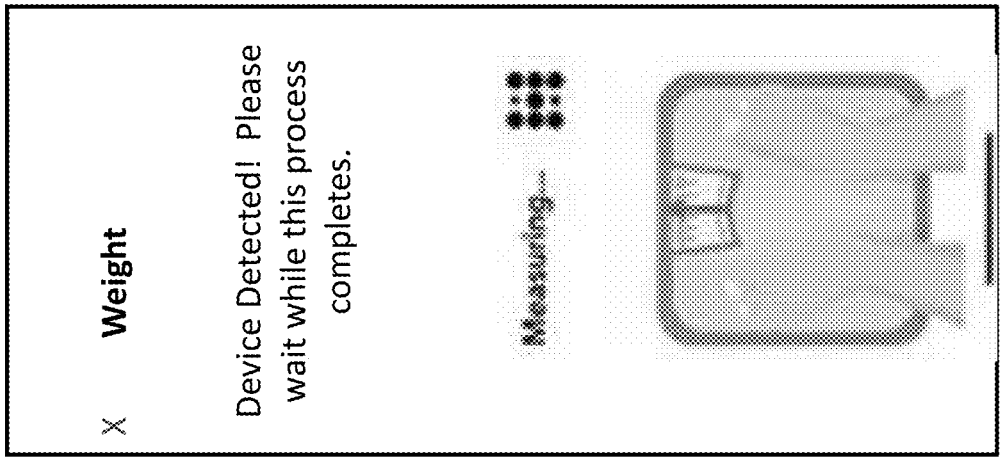
FIGS. 5a, 5b, and 5c are views of health measurement instructions provided by the health application.
Figure 5B:
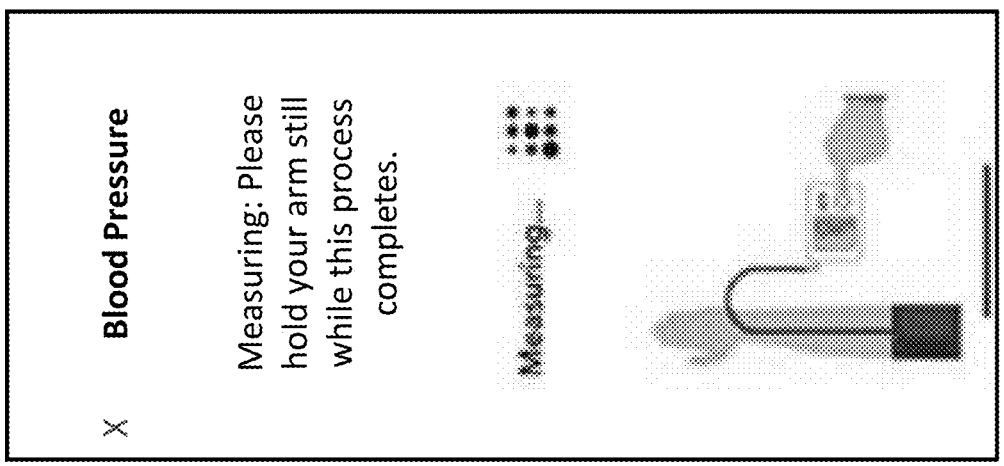
Figure 5A:
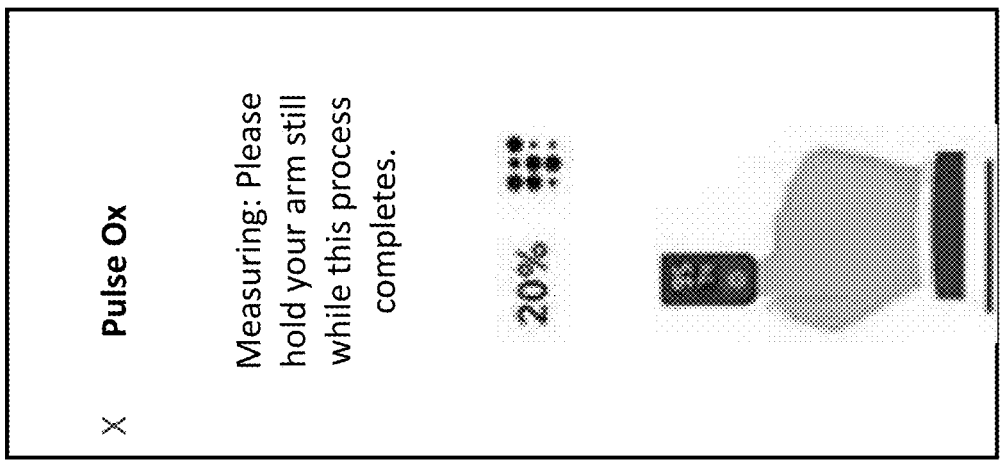

FIGS. 5a, 5b, and 5c are views of health measurement instructions provided by the health application. FIG. 5a is a view of health measurement instructions for a pulse oximeter, which is a device that can be used to measure a patient's blood oxygen levels. The instructions can include (i) the name of the health measurement ("Pulse Ox"), (ii) an image or animation demonstrating how to use the pulse oximeter on a finger, (iii) textual instructions that indicate that the patient should "hold still while this process completes," and (iv) a completion percentage for the process.

FIG. 5b is a view of health measurement instructions for a blood pressure device. The instructions can include (i) the name of the health measurement ("Blood Pressure"), (ii) an image or animation demonstrating how to position the blood pressure cuff on an arm, (iii) textual instructions that indicate that the patient should "hold your arm still while this process completes," and (iv) a message indicating that the measurement is in progress.

FIG. 5c is a view of health measurement instructions for a scale. The instructions can include (i) the name of the health measurement ("Weight"), (ii) a picture of the device, (iii) textual instructions indicating that the patient should "wait while this process completes," and (iv) a message indicating that the measurement is in progress.

The instructions can be more thorough if the health sensor is complex to use or unfamiliar to many patients. To that end, the instructions can include a number of steps. The user device may provide instructions for a particular step only after the preceding step is complete. For example, if the health sensor is a blood pressure device, the user device may first instruct the patient to place the blood pressure cuff on his or her arm. The user device may provide instructions for a next step only after the patient has properly positioned the blood pressure cuff on his or her arm. The sensor integration module can determine if the patient properly positioned the blood pressure cuff on his or her arm by communicating with the blood pressure cuff over the network. The blood pressure cuff can have sensors that can detect the position of the blood pressure cuff relative to the patient's arm, and the blood pressure cuff can transmit a signal to the health application that indicates whether or not the cuff is properly positioned. The sensor integration module may only proceed to provide instructions for the next step in the process if the signal indicates that the blood pressure cuff is properly positioned on the patient's arm.

Alternatively, the instructions can be simple if the health sensor is easy to use and generally familiar to patients. For example, if the health sensor is a scale, the instructions may simply show an image of a scale.

Heath Sensor Operation

The sensor integration module for a health sensor can also include procedures that, when executed, control operation of the health sensor. The sensor integration module can cause the user device to transmit control signals to the health sensor when particular conditions are met. For example, if the health sensor is a scale, the sensor integration module can transmit a signal to the scale that causes the scale to measure the patient's weight when a force is applied to the scale. As another example, if the health sensor is a blood pressure device, the sensor integration module can transmit a signal to the blood pressure cuff that causes it to inflate when the sensor integration module determines that the blood pressure cuff is properly positioned on the patient's arm. By controlling operation of the health sensor, the sensor integration module can minimize user input that is required to operate the health sensor.

In some cases, the health sensor may not need to receive control signals from the user device, but can instead operate independently. For example, a heart rate monitor may begin collecting data as soon as it is turned on.

The health application can initiate pairing, provide health measurement instructions to the patient, and operate the health sensors in response to a single user input in the health application. In some cases, no further patient interaction with the health application may be required.

Data Synchronization & Error Handling

The sensor integration module can also handle communication between the user device and the health sensor, and between the health sensor and the platform. As previously mentioned, the sensor integration module can cause the user device to transmit control signals to the health sensor. The sensor integration module can also include processing logic for requesting data from the health sensor. The data can include data about whether the health sensor is being used properly, and data generated as a result of taking a health measurement, e.g., a blood pressure, a blood oxygen level, or a weight.

In some cases, a patient may move the user device out of communication range of the health sensor while health measurement data is being transmitted to the user device. The sensor integration module can determine that the received data is incomplete, and can transmit a request to the health sensor to send the remaining data once the user device is again within range and paired to the health sensor.

In some cases, a patient may use a health sensor incorrectly, which may cause the sensor integration module to receive invalid data. The sensor integration module can determine that particular data is invalid by comparing it to an expected format, range, or characteristic of the data. If the data does not satisfy the expected format, range, or characteristic, the sensor integration module can cause the user device to provide new or revised instructions to the patient about how to use the health sensor.

The sensor integration module can also handle communication between the user device and the platform, on which the health measurement data may be permanently stored.

Figure 6:
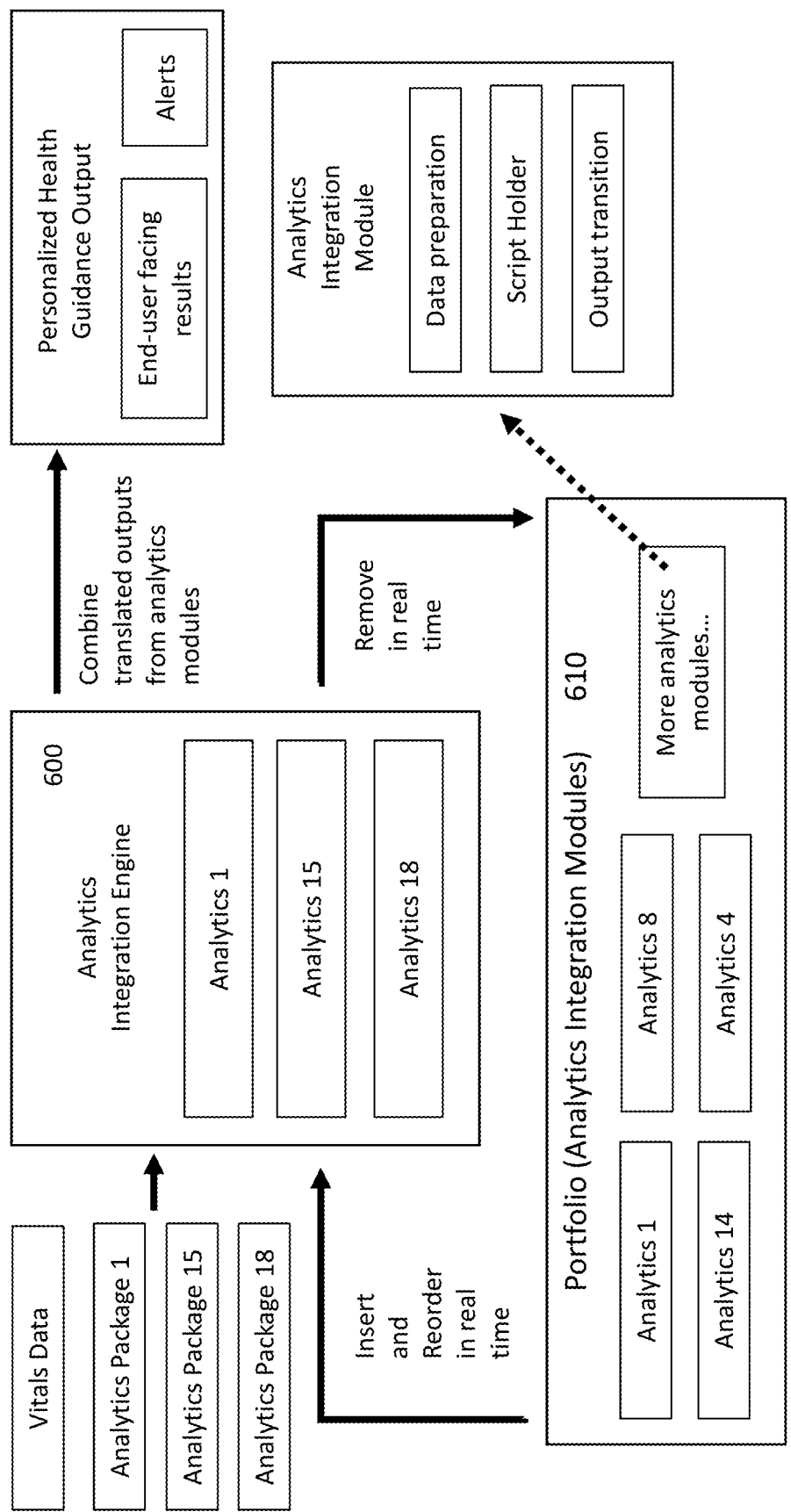
FIG. 6 schematically illustrates an analytics layer of the population health system.

FIG. 6 schematically illustrates an analytics layer of the population health system described herein. The analytics layer can be implemented on the platform 110 described in reference to FIG. 1. The analytics layer can include an analytics integration engine 600. The analytics integration engine 600 can be configured to modularly integrate any combination of third-party analytics and algorithms to create customized health and behavioral guidance for a patient. Examples of such guidance can include medicinal methods (e.g., optimized insulin dosage amounts or arterial fibrillation detection) or behavioral methods (e.g., optimized sleep patterns, caloric intake, or exercise habits). Like the guided workflow engine 300, the analytics integration engine 600 can select from a portfolio of analytics integration modules 610 analytics integration modules that correspond to analytics selected by a health care provider for the patient. Alternatively or additionally, a machine learning model trained on data from the patient-facing layer can automatically select appropriate analytics integrations modules. The analytics integration modules can be inserted and reordered in the analytics workflow in real-time. The analytics integration engine 600 can receive data from the patient-facing layer to inform the third-party analytics and algorithms. For example, a third-party dieting application can use weight data from the patient-facing layer to adjust meal recommendations. The analytics layer and the patient-facing layer can be combined to form a complete end-to-end solution that can produce outcomes that adapt to each patient's changing health state. The outcomes can then be relayed to care providers, health coaches, and the patients themselves. The ability of the analytics integration engine 600 to combine any combination of in-house or third party analytics modules can ensure that a large combination of methods are simulated, tested, and optimized to ensure maximum effect on patient outcomes.

Figure 8:
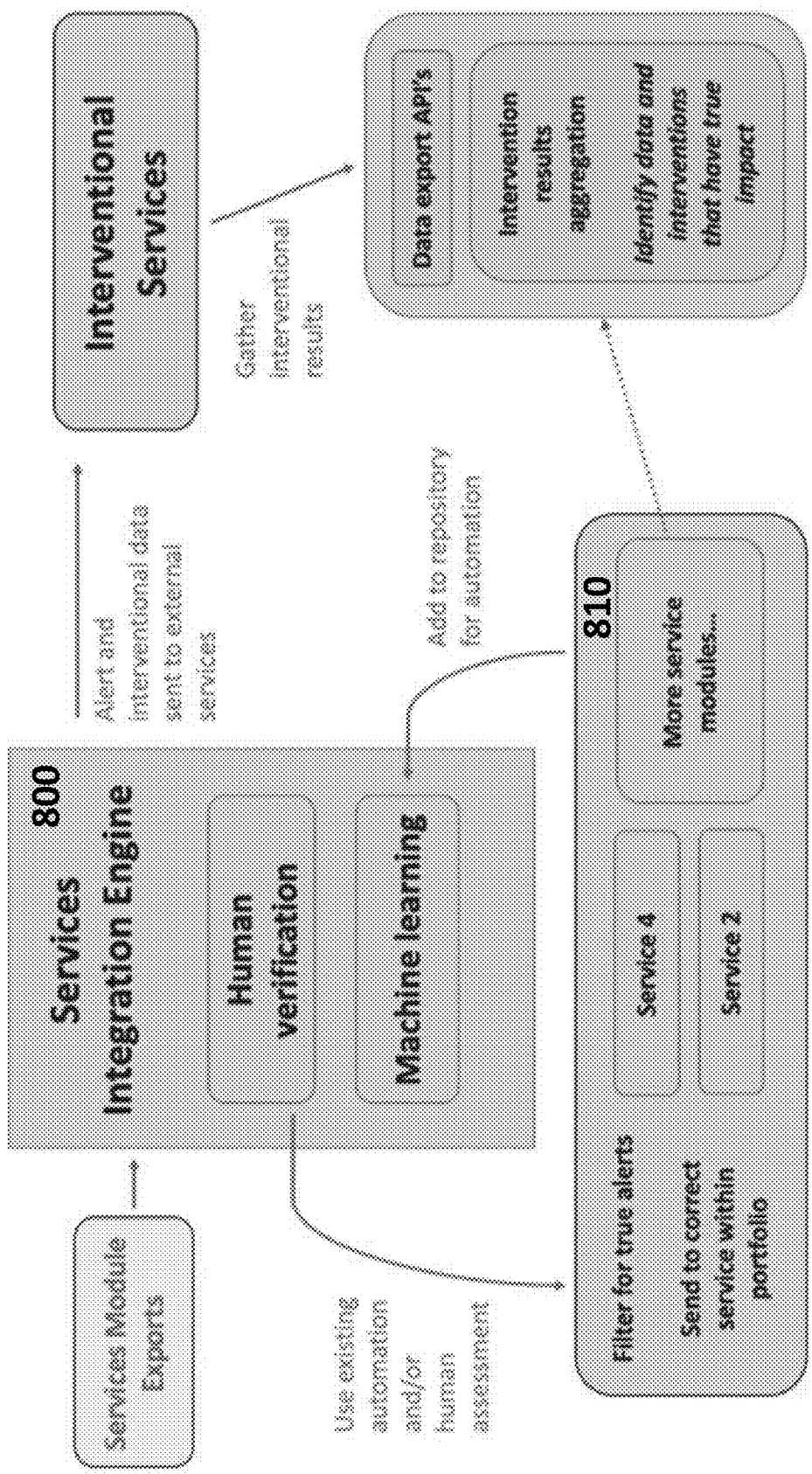
FIG. 8 schematically illustrates a service layer of the population health system.

FIG. 8 schematically illustrates a service layer of the population health system described herein. The service layer, like the analytics layer, can be implemented on the cloud-based platform 110 described in reference to FIG. 1. In general, the service application layer can receive processed health measurement data from the analytics layer, determine whether the processed health measurement data satisfies an alert criterion, and alert a health care service if the data does satisfy the alert criteria. "Health care services" as used herein can include emergency services, e.g., ambulance services, or a patient's primary care physician, pharmacist, nutritionist, or exercise coach, to name a few examples.

The service layer can include a services integration engine 800. The services integration engine 800 can select appropriate service modules for a particular patient from a portfolio of service modules 810. The service modules can receive processed health measurement data, e.g., analytics outputs, from the analytics layer, determine whether the processed health measurement data satisfies an alert criterion, and alert the corresponding health care service if the data does satisfy the alert criteria.

In an example, a patient may use the patient-facing layer of the health application and an electrocardiograph to measure the patient's heart activity. The health application can transmit the raw data to the analytics layer, where a heart activity algorithm can analyze the raw data. The services integration module 800 can provide the output of the algorithm to one or more service modules, e.g., a service module for an ambulance service and a service module for the patient's primary care physician. If the output of the algorithm satisfies an alert criterion for a particular service module, that service module can alert the corresponding service. The service modules can have different alert criteria. For example, the alert criterion for a service module for an ambulance service may correspond to an analytics output that indicates a life-threatening abnormality. In the case of a heart activity algorithm, such an analytics output may be a particular confidence that a heart attack is occurring. On the other hand, the alert criterion for a service module for the patient's primary care physician may correspond to an analytics output that indicates a non-life-threatening abnormality. In the case of a heart activity algorithm, such an analytics output may be a particular confidence that the patient has arterial fibrillation, but that a heart attack is not presently occurring).

The services integration engine 800 can use machine learning methods to select appropriate service modules for a patient. Initially, service modules may be selected or verified by a human. In time, however, the service layer can aggregate analytics outputs and data about service alerts that were generated as a result of the analytics outputs. A health care provider can determine, based on the health analytics outputs, whether the service alerts were actually necessary. This data can serve as training data for a supervised machine learning model. The machine learning model can determine that particular services are or are not necessary for a particular patient and add or remove those services from the patient's instance of the service layer.

Figure 9:
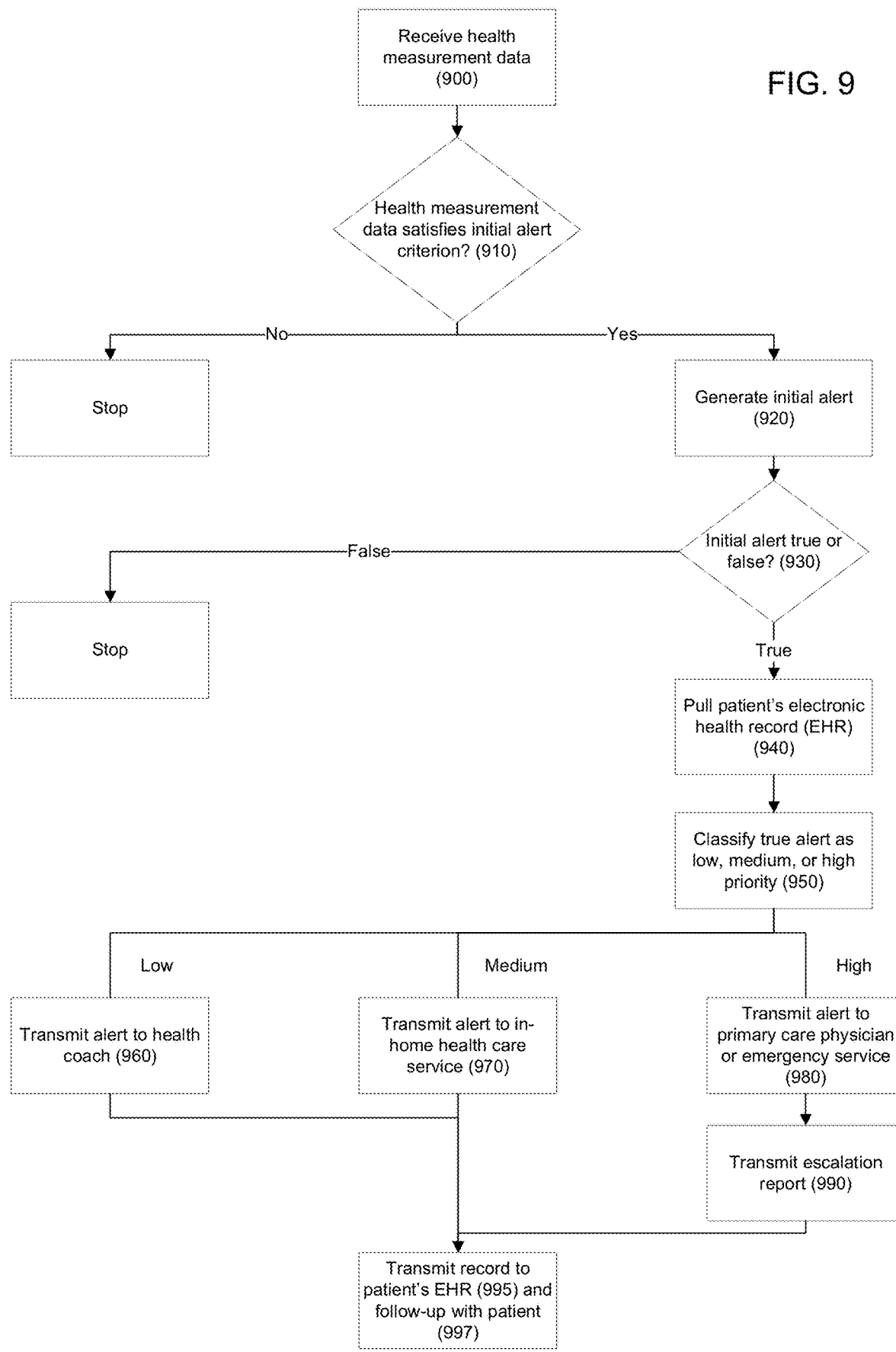
FIG. 9 is a flow chart of a process for processing alerts and prompting patient interventions.

FIG. 9 is a flow chart of an example process for processing alerts and prompting patient interventions. The process can be performed by the analytics layer described in reference to FIG. 6.

The analytics layer can receive health measurement data from a patient's user device (900). The health measurement data can indicate the patient's heart rate or rhythm, blood pressure, blood oxygen level, body weight, body temperature, or blood sugar level, for example.

The analytics layer can determine whether the health measurement data satisfies an initial alert criterion (910). The initial alert criterion can be a minimum or maximum value. For example, the initial alert criterion can be a minimum or maximum heart rate, a minimum or maximum blood pressure, a minimum or maximum blood oxygen level, a minimum or maximum body weight, a minimum or maximum body temperature, or a minimum or maximum blood sugar level. In some cases, the initial alert criterion can be the existence or occurrence of a particular feature in the health measurement data (e.g., a particular heart rhythm). Alternatively, the initial alert criterion can be a magnitude or percent deviation from a baseline health measurement for the patient.

The initial alert criterion can be an alert criterion that is applicable to the general population. For example, the initial alert criterion for blood oxygen level can be a blood oxygen level below which the medical community generally recognizes as unsafe. Alternatively, the initial alert criterion can be an alert criterion that is applicable to a sub-population to which the patient belongs. For example, if the patient has chronic obstructive pulmonary disorder (COPD), the initial alert criterion for blood oxygen level for the patient can be a blood oxygen level below which the medical community recognizes as being unsafe for patients with COPD. Patients with COPD may have lower safe blood oxygen levels than patients without COPD. The initial alert criterion can instead be patient-specific. For example, a patient that typically has blood oxygen levels below the normal range can have a lower initial alert criterion. The use of different initial alert criteria for different sub-populations and patients can reduce the generation of false alerts.

The initial alert criterion can be static as described above, or it can be dynamic. For example, an algorithm can determine the initial alert criterion in real-time based on the patient's previous health measurements, diagnostic and medication history, current health state, current diet and exercise levels, the validity of previous alerts as determined by a health care professional or interventional service, and other factors. The algorithm can be a machine learning algorithm.

Figure 10A:
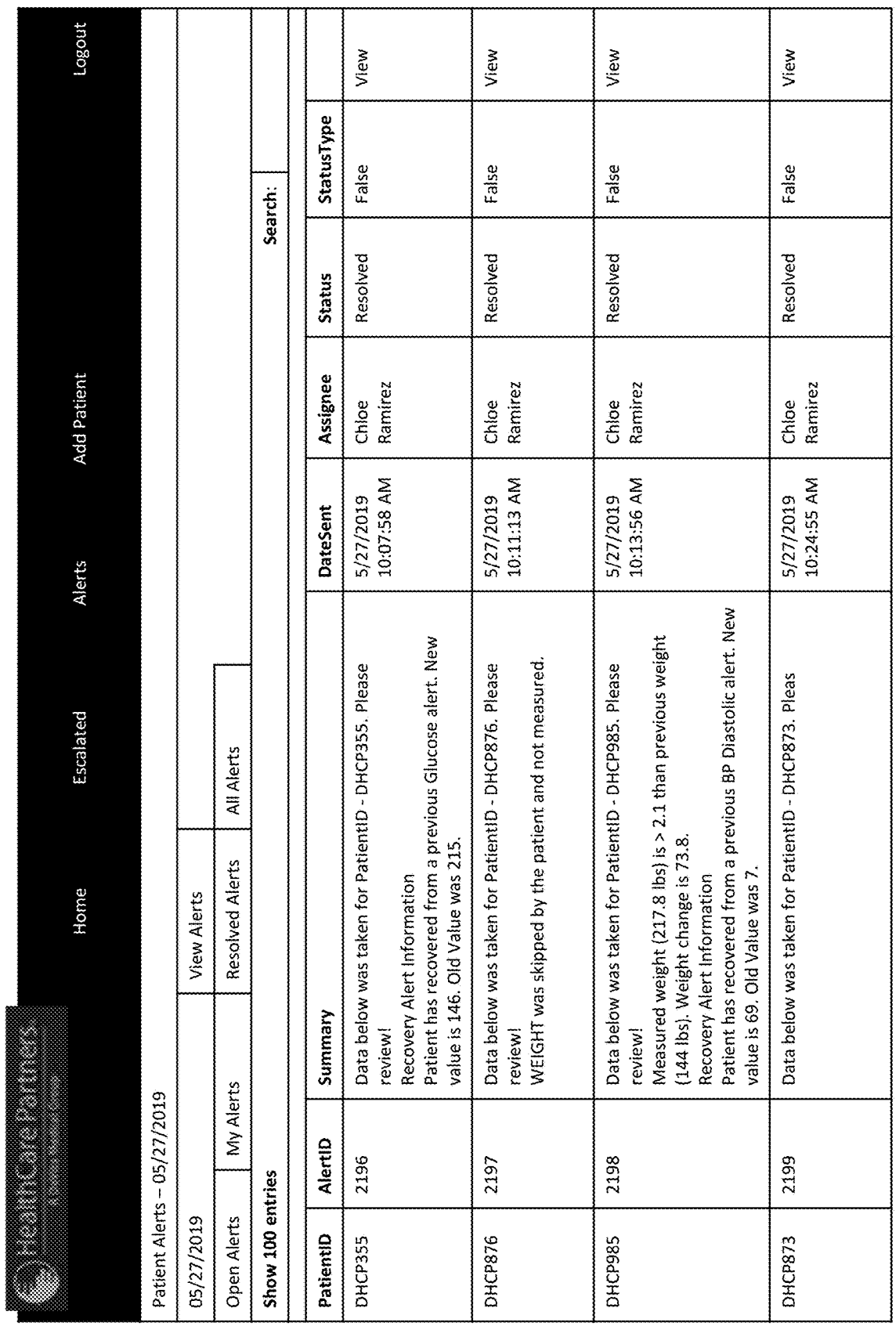

If the health measurement data does satisfy the initial alert criterion, the analytics layer can generate an initial alert (920). Generating the initial alert can involve pushing a record of the health measurement data to a dashboard on the analytics layer. FIG. 10A is an image of such a dashboard. The dashboard can be a graphical user interface viewable by human agents that can assess whether the alert is true or false, and if the alert is true, the severity of the alert. The human agents can be trained medical professionals (e.g., health coaches, technicians, or board-certified nurses or doctors). The record of the health measurement data that is pushed to the dashboard can include the health measurement itself, the time the measurement was taken, and previous health measurements for the patient. The dashboard can allow the human agent to classify the alert as true or false and take follow-up actions if the alert is classified as true. The dashboard can also have a communication interface that allows the human agent to contact the patient through the health application. The human agent can ask the patient, for example, to take the health measurement again or whether any extenuating circumstances may have affected the health measurement. The patient, using a corresponding communication interface in the health application, can confirm that he or she will take the health measurement again or explain any extenuating circumstances. For example, the patient may explain that his heart rate is high because he was exercising immediately prior to the health measurement; that his blood sugar is high because he recently ate; or that his blood oxygen level is low because he briefly stopped using his oxygen machine to use the restroom. The human agent can use this information is determining whether the alert is true or false. The dashboard will be described in greater detail below.

After the analytics layer generates an initial alert, the analytics layer, a human agent or both can determine whether the alert is true or false (930). In some cases, the analytics layer can resolve alerts without input from a human agent. The analytics layer can determine, for example, that although the health measurement data for the patient satisfied an initial alert criterion for the general population, the data did not satisfy a less restrictive secondary alert criterion for the patient. Similarly, the analytics layer may determine that although the health measurement data for the patient satisfied an initial alert criterion, the data did not depart a sufficient amount from the patient's baseline health measurement to constitute a true alert. In such a case, the analytics layer may again resolve the alert without input from a human agent.

The analytics layer can transmit a communication to the patient's user device to ask for additional information. For example, if the analytics layer detects an anomaly or error in the health measurement data, the analytics layer can transmit a message to the patient's user device that asks the patient to retake the health measurement. Alternatively, the analytics layer can reconfigure the health application workflow in real-time to simplify the health measurement process for the patient.

In some cases, the analytics layer can perform an initial assessment of the alert, but the platform may require that a human agent review the alert before it can be resolved. In still other cases (e.g., when the alert relates to a critical health measurement), a human agent may be prompted to perform a first review of the alert. The platform can automatically prioritize alerts and assign alerts to particular human agents.

Figure 10B:

Human agents can review initial alerts on the dashboard depicted in FIG. 10A. The dashboard can display alerts in a table. Each row in the table can be a different alert. The columns in the table can depict different information about each alert, e.g., a patient name or patient ID, alert ID, a summary of the health measurement that resulted in the alert and previous health measurements for the patient, the date and time the health measurement was taken, the human agent to which the initial alert was assigned, whether the alert has been resolved, and the status of the resolved alert. An alert can include a link to the patient's profile on the dashboard. The profile can include the patient's medical history and previous health measurement data. The previous health measurement data may be depicted in a graph so that the human agent can easily see the patient's progress over time. The dashboard can allow the human agent to record notes about the alert, resolve the alert as either true or false, and if true, escalate the alert to a health care provider (FIG. 10B and FIG. 10C). Notes and actions taken by the human agent can be preserved to create an audit trail. The notes and actions can also be incorporated into the patient's electronic health record (EHR).

If the analytics layer or a human agent determines that the initial alert is true, the analytics layer can automatically pull the patient's EHR into the platform (940). FIG. 10D is an image of a patient's EHR as it might be displayed on the platform.

Using the health measurement data that resulted in the alert, the patient's previous health measurements, and the patient's EHR, the analytics layer or a human agent can classify the alert as a low, medium, or high priority (950).

The analytics layer can use a machine learning algorithm to classify the alert as low, medium, or high priority. The machine learning algorithm can receive as input the health measurement data that caused the alert to be generated, the patient's previous health measurement data, and data from the patient's EHR, e.g., clinical test results, medication history, family history, diagnoses, and the like. The machine learning algorithm can be trained to accurately classify alerts based on these inputs. The machine learning algorithm can be trained to recognize latent features (e.g., correlated inputs) that result in a particular classification.

The training data for the machine learning algorithm can be previous health measurements that resulted in true alerts and the actual priority of those alerts as determined by a health care professional, along with other features of the patient's medical history. Such training data can be used to tune the parameters of the machine learning model to more accurately predict the priority of future alerts. The machine learning algorithm can be trained on data from the general population, data from a sub-population to which to the patient belongs, or data from the patient alone. In some cases, the machine learning model can be trained on data from the general population but conditioned on data from the patient.

The machine learning algorithm can be a supervised machine learning algorithm or an unsupervised machine learning algorithm. The machine learning algorithm can be a regression algorithm, a Naive Bayes classifier, a support vector machine, a clustering algorithm, a decision tree algorithm, a random forest, or a neural network.

Neural networks may be well-suited to classify alerts as low, medium, or high priority. Neural networks are machine learning models that can use multiple layers of operations to predict one or more outputs from one or more inputs. The input layer of a neural network can receive one or more features that may be indicative of the desired output. Neural networks can include one or more hidden layers situated between the input layer and an output layer. The nodes of the input layer can be connected to the nodes of the first hidden layer, and the nodes of the first hidden layer can additionally be connected to nodes in a subsequent hidden layer or the output layer. Each connection can have a weight. A node's output (i.e., activation) can be based on the inputs to the node (i.e., the activations in the previous layer) and the weights of the incoming connections. The connections and weights can define a complex function. The output layer of a neural network can have one node for each of the possible outputs (e.g., classifications). The relative activations of the nodes in the output layer can represent the predicted classification.

Training a neural network can involve adjusting the connection weights until the neural network accurately predicts outputs at an acceptable rate. Adjusting the connection weights can involve providing inputs to the neural network for which an output is known. The predicted output generated by the neural network can be compared to the known output to compute the value of an error-function. The error can be "back-propagated" through the network. That is, the weight of each connection can be adjusted to reduce the value of the error function by some small amount. After repeating this process for a sufficiently large number of training cycles, the neural network can converge to some state where the error of the calculations is small.

Additionally or alternatively, a human agent can review and classify the true alert as being a low, medium, or high priority alert. In some cases, one of the machine learning algorithms described above can make an initial classification. If the initial classification is medium or high, a human agent can review the alert to confirm that the classification is correct and expedite patient intervention.

If the analytics layer and/or a human agent determines that the true alert is a low-priority alert, the analytics layer can transmit the alert to an in-house medical professional or a behavioral intervention service (e.g., health coach) (960). The in-house medical professional or health coach can then reach out to the patient (e.g., via phone, text, email, or through application) to address the cause of the alert.

If the analytics layer and/or a human agent determines that the true alert is a medium-priority alert, the analytics layer can transmit the alert to a health care service that can conduct an in-home visit with the patient (970).

Figure 11A:
FIGS. 11A and 11B are images of an example escalation report generated by the population health system.
Figure 11B:
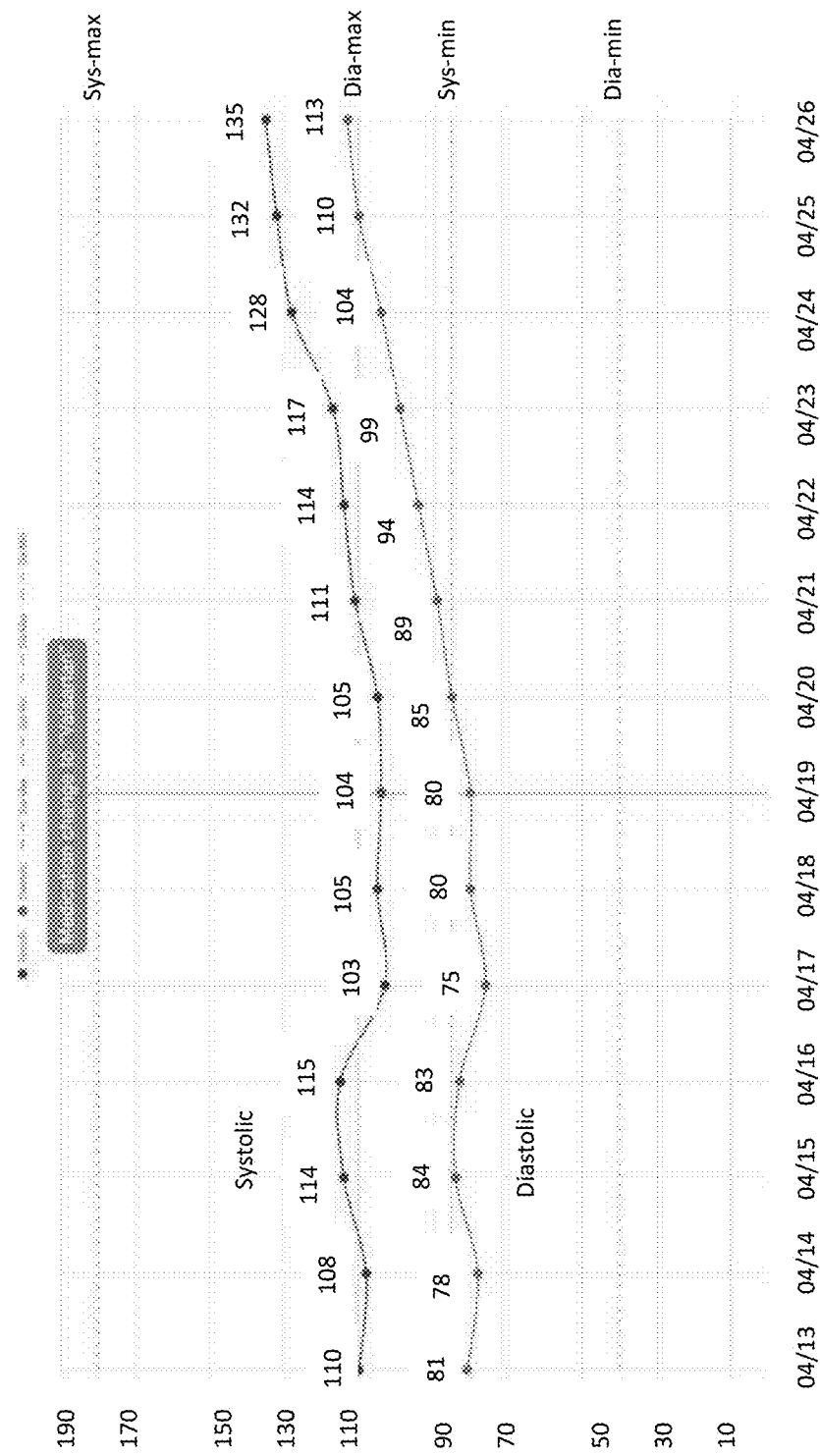

If the analytics layer and/or a human agent determines that the true alert is a high-priority alert, the analytics layer can transmit the alert directly to the patient's primary care physician or an emergency service (980). In addition to escalating the alert, the analytics layer can automatically generate and transmit an escalation report to the patient's primary care physician (990). FIG. 11A is an image of a first page of an example escalation report. The escalation report can include the patient's name, address, contact information, height and weight, date of birth and age, medication history, and diagnostic history. The escalation report can also include a summary of the health measurement that caused the alert to be generated ("Patient first diastolic value of the day was 112 mmHG, and repeat measurement yielded 114 mmHG.") The escalation report can also include a summary of an investigation conducted by a human agent, if applicable, ("Patient's blood pressure has been going up steadily since medication change last week.") and any feedback that the patient provided about his or her health state ("Feeling hungrier and dizzier since last week—more tired as well. Drank 3 beers last night.") The escalation report may also include a graph of the relevant health measurement over time (FIG. 11B). In some cases, the graph may include a marker that indicates the occurrence of an event, e.g., a hospitalization or a medication change. The marker can add context the patient's measurements. The patient's primary care physician can use this report to quickly and easily make health care decisions. The analytics layer can automatically generate the escalation report by integrating data stored on the platform with data from the patient's EHR.

The analytics layer can transmit a record of the alert and the subsequent intervention to the patient's EHR (995). The analytics layer can also generate and transmit tasks, e.g., future appointments or tests, to the patient's EHR. Escalating alerts and interventions in this tiered-fashion can reduce health care costs and hospitalizations.

After the intervention is complete, a human agent can follow-up with the patient through the health application to ensure that proper treatment was provided (997). If necessary, the human agent can re-escalate the alert to a health care provider.

Figure 12:
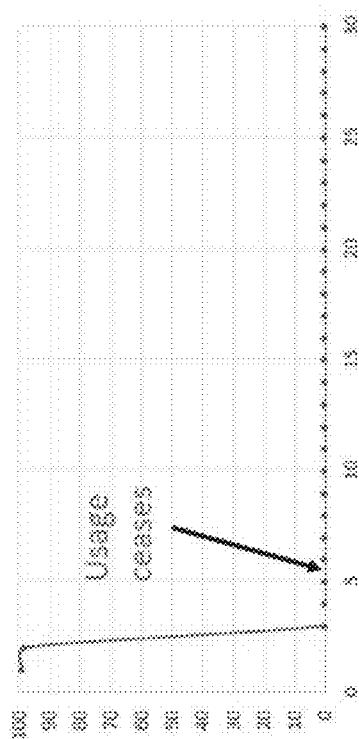
FIG. 12 shows the results of a study that compared the efficacy of the population health system with various other single-sensor platforms.

FIG. 12 shows the results of a study that compared the efficacy of the population health system described herein with various other single-sensor platforms. For each patient, the population health system was configured to have a heart rate sensor, a pulse oximeter, a scale, and a blood pressure device, while the single-sensor platforms were configured to have only a pulse oximeter. Only 30% of patients using the various other single-sensor platforms were able to take unassisted measurements, while 94% of patients using the population health system described herein were able to take unassisted measurements. This data demonstrates how the guided workflow in the health application can result in greater patient adherence to health measurement routines. As a result of this increased adherence, the population health system can reduce hospitalizations of patients by 78% due to early intervention.

Figure 13:
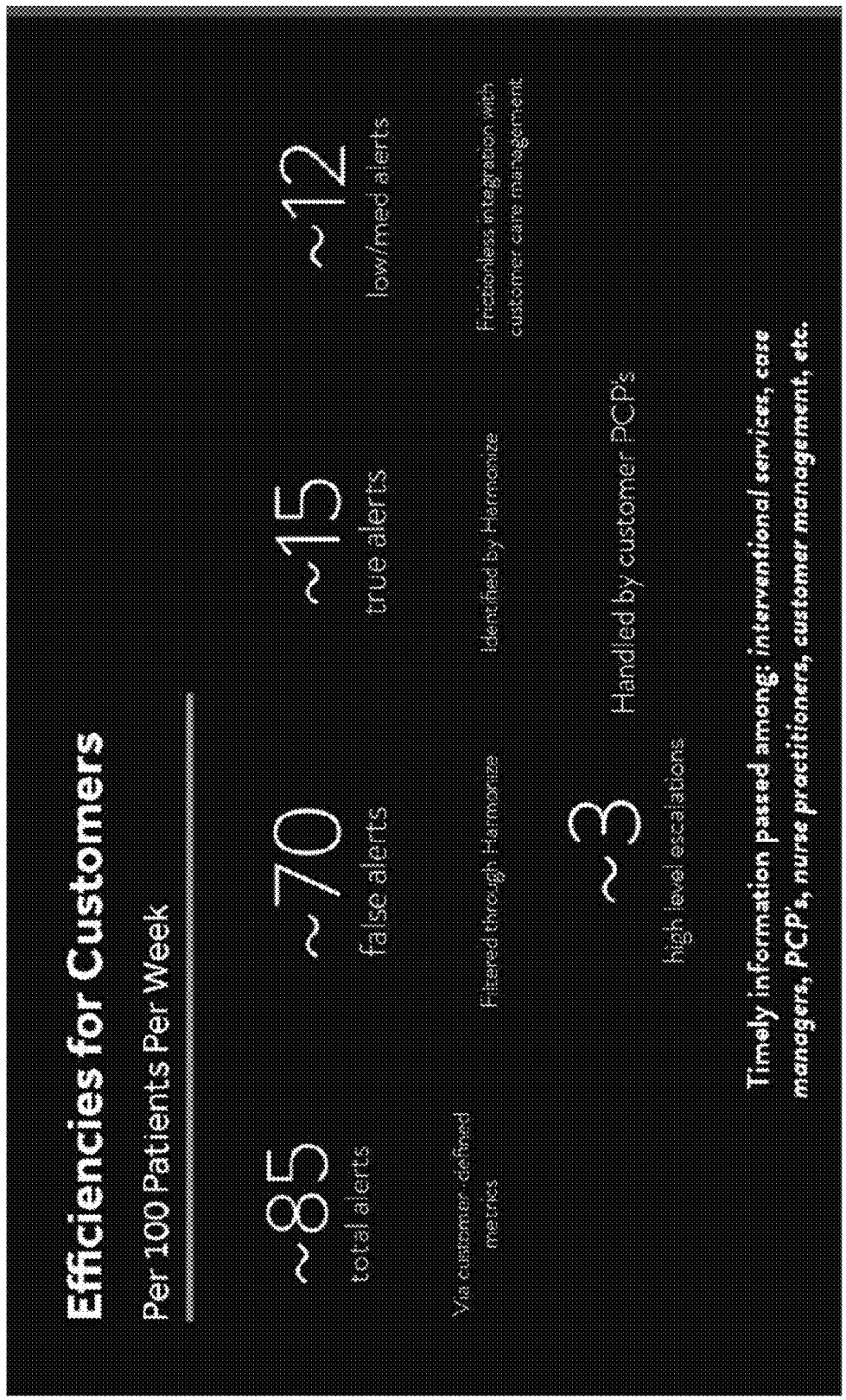
FIG. 13 shows how the alert processing system results in efficiencies for customers.

FIG. 13 shows how the alert processing system described in reference to FIG. 9 results in efficiencies for customers. The population health system may generate approximately 85 initial alerts per 100 patients per week. The initial alerts may be based on customer-defined metrics that are very restrictive. The population health system may classify approximately 70 of the 85 initial alerts as false, leaving approximately 15 true alerts. The population health system may classify approximately 12 of the 15 true alerts as low-priority or medium-priority alerts that can be handled without intervention by the patients' primary care physicians. This leaves only approximately three alerts that are escalated to the patients' primary care physicians. This alert filtering and tiered-escalation process can save customers time and money and ensure early intervention for alerts that are truly critical.

Computer Control Systems

Figure 7:
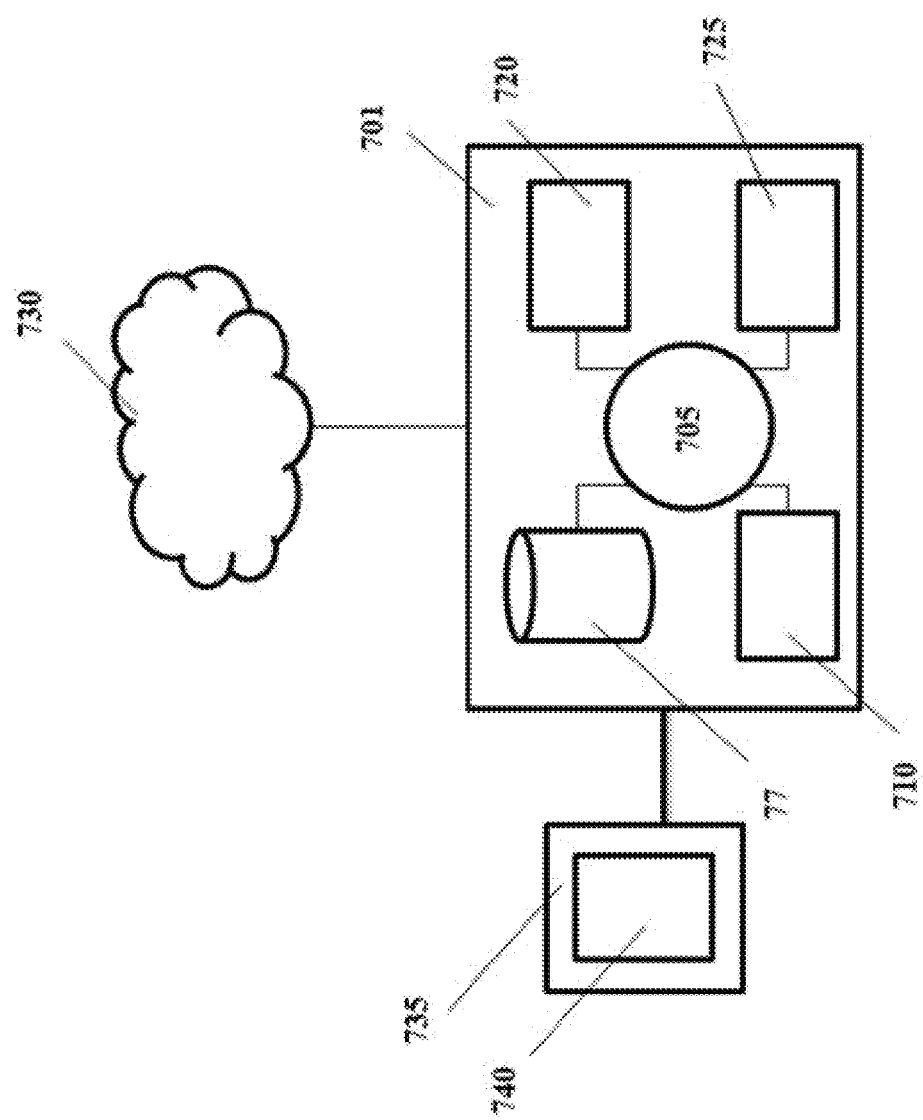
FIG. 7 schematically illustrates a computer control system that is programmed or otherwise configured to implement systems and methods provided herein.

The present disclosure provides computer control systems that are programmed or otherwise configured to implement methods of the disclosure. FIG. 7 shows a computer system 701 that is programmed or otherwise configured to control the user devices or health sensors described in this disclosure.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, information regarding the manufacturing of the thermoelectric unit. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system comprising one or more computers and one or more storage devices storing instructions that are operable, when executed by said one or more computers, to cause said one or more computers to perform operations comprising:
    (a) receiving healthcare prescription information associated with a user;
    (b) generating, based at least in part on said healthcare prescription information, data defining (1) a plurality of health sensors, (2) an order in which said plurality of health sensors are to be used by said user to take different physiological measurements, and (3) a frequency at which said user is to use said plurality of health sensors to take said different physiological measurements;
    (c) encoding said data from (b) into a single visual code; and
    (d) generating, in real-time and based on an image of said single visual code captured using a user device, application logic for a health application configured to run on said user device, wherein said application logic (1) comprises a different pairing procedure for pairing each of said plurality of health sensors to said user device and (2) defines user-specific instructions for taking said different physiological measurements using said plurality of health sensors, wherein said user-specific instructions are customized for said user based on said healthcare prescription information, and wherein said application logic is configured to cause, in response to at most one user input from said user on said user device, said user device to:
        automatically and operatively couple to said plurality of health sensors, thereby establishing wireless communication between said user device and each of said plurality of health sensors, and
        provide said user-specific instructions to said user of said user device through a graphical interface of said user device, wherein said user-specific instructions are provided to said user sequentially in said order from (b).

2. The system of claim 1, wherein said operations further comprise: (i) obtaining resultant data from said user device, wherein said resultant data comprises data collected as a result of said user taking said different physiological measurements, (ii) determining that said resultant data satisfies an alert criterion, and (iii) in response to said determination, transmitting an alert to a health care provider of said user.

3. The system of claim 2, wherein said operations further comprise:
    prior to transmitting said alert, classifying said alert as a low-priority alert, a medium-priority alert, or a high-priority alert, and wherein transmitting said alert to said health care provider comprises: (i) transmitting a low-priority alert to a behavior intervention service, (ii) transmitting a medium-priority alert to an in-home health service, and (iii) transmitting a high-priority alert to a primary care physician of said user or an emergency service.

4. The system of claim 3, wherein transmitting said high priority alert to said primary care physician or said emergency service comprises transmitting an escalation report to said primary care physician or said emergency service.

5. The system of claim 4, wherein said escalation report comprises a subset of medical history data for said patient and said resultant data.

6. The system of claim 3, wherein said classifying comprises:
    obtaining medical history data for said patient; and using a trained machine learning algorithm to process said resultant data and said medical history data to generate said classification.

7. The system of claim 6, wherein said trained machine learning algorithm is selected from the group consisting of: a regression algorithm, a Naive Bayes classifier, a support vector machine, a clustering algorithm, a decision tree algorithm, a random forest, or a neural network.

8. The system of claim 1, wherein said single visual code comprises a barcode or a quick response (QR) code.

9. The system of claim 1, wherein said plurality of health sensors are selected from the group consisting of a heart rate monitor, a blood pressure cuff, a pulse oximeter, a scale, a thermometer, and a glucose meter.

10. The system of claim 1, wherein generating said application logic comprises obtaining, from a configuration file, a universally unique identifier for each of said plurality of health sensors.

11. The system of claim 1, wherein said coupling comprises scanning and identifying said plurality of health sensors.

12. The system of claim 1, wherein said application logic is further configured to cause said user device to transmit control signals to said plurality of health sensors to control operation of said plurality of health sensors while said user is taking said different physiological measurements.

13. The system of claim 1, wherein said health application comprises a communication interface configured to allow said user to communicate with a health care provider.

14. The system of claim 1, wherein said user-specific instructions comprise animations that indicate how to use said plurality of health sensors.

15. The system of claim 1, wherein said user-specific instructions comprise audible instructions, textual instructions, or pictorial instructions.

16. The system of claim 1, wherein said application logic is configured to provide instructions for taking a physiological measurement using a health sensor after receiving valid data for a preceding physiological measurement.

17. The system of claim 16, wherein valid data comprises data falling within a predefined range or data having a predetermined characteristic.

18. The system of claim 1, wherein said application logic is configured to provide instructions for re-taking a physiological measurement after receiving invalid data for said physiological measurement.

19. The system of claim 1, wherein said application logic is further configured to cause said user device to generate reminders to take said different physiological measurements at said frequency.

20. The system of claim 1, wherein said operations further comprise:
storing resultant data from said user device on a cloud-based platform, wherein said resultant data comprises data collected as a result of said user taking said different physiological measurements.

21. The system of claim 20, wherein said cloud-based platform comprises a dashboard configured to allow a health care provider to review said resultant data.

22. The system of claim 2, further comprising:
receiving data indicating a validity of said alert from said health care provider; and
adjusting said alert criterion based on said data indicating said validity of said alert.

23. A kit comprising:
a plurality of health sensors; and
a user device configured to run a health application, wherein said health application is configured to cause said user device to:
obtain an image of a single visual code, which single visual code encodes data defining (1) a plurality of health sensors, (2) an order in which said plurality of health sensors are to be used by a user to take different physiological measurements, and (3) a frequency at which said user is to use said plurality of health sensors to take said different physiological measurements;
generate, in real-time and based on said image of said single visual code, application logic configured to run on said user device, wherein said application logic (1) comprises a different pairing procedure for pairing each of said plurality of health sensors to said user device and (2) defines user-specific instructions for taking said different physiological measurements using said plurality of health sensors, wherein said user-specific instructions are customized for said user, and wherein said application logic is configured to cause, in response to at most one user input from said user on said user device, said user device to
automatically and operatively couple to said plurality of health sensors, thereby establishing wireless communication between said user device and each of said plurality of health sensors, and
provide said user-specific instructions to said user of said user device through a graphical interface of said user device, wherein said user-specific instructions are provided to said user sequentially in said order.

24. A method comprising:
(a) receiving healthcare prescription information associated with a user;
(b) generating, based at least in part on said healthcare prescription information, data defining (1) a plurality of health sensors, (2) an order in which said plurality of health sensors are to be used by said user to take different physiological measurements, and (3) a frequency at which said user is to use said plurality of health sensors to take said different physiological measurements;
(c) encoding said data from (b) into a single visual code; and
(d) generating, in real-time and based on an image of said single visual code captured using a user device, application logic for a health application configured to run on said user device, wherein said application logic (1) comprises a different pairing procedure for pairing each of said plurality of health sensors to said user device and (2) defines user-specific instructions for taking said different physiological measurements using said plurality of health sensors, wherein said user-specific instructions are customized for said user based on said healthcare prescription information, and wherein said application logic is configured to cause, in response to at most one user input from said user on said user device, said user device to:
automatically and operatively couple to said plurality of health sensors, thereby establishing wireless communication between said user device and each of said plurality of health sensors, and
provide said user-specific instructions to said user of said user device through a graphical interface of said user device, wherein said user-specific instructions are provided to said user sequentially in said order from (b).

25. The system of claim 1, wherein said user device is a mobile device.

26. The system of claim 25, wherein said mobile device is not pre-configured with pairing instructions for coupling said mobile device to said plurality of health sensors.

27. The system of claim 1, wherein said user-specific instructions comprise a separate instruction for each of said plurality of health sensors, and wherein each of said separate instructions is provided one at a time.

* * * * *